United States Patent [19]
Gallant et al.

[11] Patent Number: 5,343,870
[45] Date of Patent: Sep. 6, 1994

[54] RECORDER UNIT FOR AMBULATORY ECG MONITORING SYSTEM

[75] Inventors: Stuart L. Gallant, Owings Mills; Paul R. Caron, Laurel; Walter E. Palmer, Catonsville, all of Md.; David J. Lubocki, Bellevue, Wash.

[73] Assignee: Quinton Instrument Company, Seattle, Wash.

[21] Appl. No.: 790,035

[22] Filed: Nov. 12, 1991

[51] Int. Cl.⁵ .............................................. A66B 5/04
[52] U.S. Cl. .................................................... 128/711
[58] Field of Search ............................... 128/702–704, 128/710–711

[56] References Cited
U.S. PATENT DOCUMENTS 3,913,567 10/1975 Streckmann .................... 128/711
4,685,708 7/1987 Ambos et al. .................... 128/703
5,205,295 4/1993 Delmor et al. ................... 128/711
5,224,486 7/1993 Lerman et al. .................... 128/696
5,238,001 8/1993 Gallant et al. ..................... 128/700

*Primary Examiner*—William E. Kamm
*Attorney, Agent, or Firm*—Andrew J. Beck; Montgomery W. Smith; Gene B. Kartchner

[57] ABSTRACT

A Holter-type recorder unit for use with an ambulatory ECG recording system is described. The recorder features real-time beat differentiation, including ST analysis and paced beat analysis of two or three channel sampled electrocardiogram data. The recorder also features real-time coding of beat morphology and summary information on cassette tape. Further, summary information for an entire analysis can be compiled and reverse recorded onto the cassette tape at the end of the analysis to allow downloading thereof into an ECG scanner while the cassette is being rewound.

63 Claims, 7 Drawing Sheets

RECORDER UNIT FOR AMBULATORY ECG MONITORING SYSTEM

BACKGROUND OF THE INVENTION

1. Field of the Invention

The invention relates generally to electrocardiography systems. More specifically, the invention relates to a Holter-type recorder capable of recording ECG wave forms in analog while simultaneously performing real-time analysis of the ECG signals and digital recording of the analysis results on cassette tape.

2. Prior Art

ECG ambulatory monitoring systems are used to obtain and analyze ECG wave forms, preferably obtained from a patient over an extended period of time. These systems usually comprise a recorder for collecting information from the patient related to the patient's ECG, and a scanner for analyzing the collected information. The scanner usually includes a playback deck for downloading information obtained by the recorder and a processing unit for analyzing the data and reporting analysis results. It has become increasingly important for scanners to be automated in order to limit the time in which it takes an operator to process, analyze and report data. It has also been increasingly important to increase the fidelity of the data collected and the accuracy, completeness and presentation of the analysis results.

Present recorders are generally designed for portable, long-term collection of electrocardiograph (ECG) data from a patient over an extended of time. The recordings made are subsequently used to detect abnormalities in the heart's electrical activity caused by a patient's routine daily activities or heightened emotional or physical states. The recordings are subsequently analyzed to form diagnoses, to assess the efficacy of treatments such as drug therapy, and to analyze pace-maker performance.

There are two basic types of ECG recording systems presently being used. The first is a "retrospective" type recording system which analyzes the collected data after completion of the collection phase. The second type is a "real-time" system which analyzes data as it is recorded. Retrospective systems typically record ECG data on a tape recorder during the collection phase, and subsequently analyze the data only after it has been downloaded into a scanner. Real-time systems typically record, analyze, and quantify data during the collection phase, and the analysis information is merely played back by the scanner once downloaded thereinto. Data collected on a real-time system is generally recorded on an electronic medium in digital form instead of on magnetic tape.

In either system, the recording unit is generally capable of amplifying ECG signals which are received from the patient through a plurality of input leads (which are attached through electrodes to various points on the patient's chest) which input either to a tape recorder (retrospective) or an electronic storage device (real-time). Real-time systems generally further include a microprocessor in conjunction with the electronic storage device for analyzing the ECG signals. Both the real-time and the retrospective type recording systems are designed to interface with a scanner, either through a magnetic tape reader, or an electronic interface, to allow downloading of the collected information for analysis, editing, storage, and/or reporting as necessary or desired.

Real-time and retrospective recording systems each have their drawbacks. For example, real-time recording systems which analyze and quantify ECG signals as they are being monitored, are limited in the amount of data they can store by the size limitations imposed by the electronic memory. Although there have been attempts to limit this problem by compressing raw data through computer algorithms, or by limiting the data stored (e.g., storing only information on ECG signals generated by aberrant heartbeats) these efforts have been less than completely successful in resolving the problem. For example, it is well known that compression algorithms can cause distortions in the data which become apparent as reduced signal fidelity when the data is later retrieved for use. Further, since it is often desirable for analysis purposes in a comprehensive clinical evaluation to be able to review all ECG wave forms as recorded over an entire monitoring period (often 24 hours), present real-time systems are often found to be less than desirable. This tradeoff of low reproducibility of signal fidelity for an increased in memory capacity is a major limitation on prior art real-time recording systems.

Retrospective recording systems, although having virtually no data storage limitations during a 24 hour ECG recording period, nevertheless suffer in the fidelity of their reproduced signal after being downloaded into a scanner. This is because the scanners often read the recordings at speeds of 60 to 240 times their actual recorded speed. These high speed play backs tend to limit fidelity by decreasing the frequency range of the recordings, and also tend to cause inaccuracy in time tracking of the tape due to tape biasing and/or misalignment of the tape on the play back head during high speed play back, and/or tape stretching due to high speed stopping and starting of the tape during analysis.

For example, when analyzing how well a heart responds to a signal from an implanted pace-maker, an inaccuracy in the timing between the pace-maker signal and the apparent response of the heart can make the difference between the perceived heart response being interpreted as physiologically acceptable or unacceptable.

Another major drawback with retrospective recording systems is the time required to rewind, download and analyze the recorded data by the scanner system, and the further time necessary to compile and generate reports based on the data.

There therefore exists a need in the art to develop a recorder which can perform real-time analysis of ECG signals from a patient over a long period of time without the necessity of compressing the data to accommodate the storage medium used. Further, there exists a need in the art to develop an ECG recorder which allows for rapid reporting of pertinent summary information usable by medical workers for purposes of early review and preliminary diagnoses.

OBJECTS AND SUMMARY OF THE INVENTION

An object of the present invention is to provide an ECG recorder which can perform real-time analysis on ECG signals received from a patient.

It is another object of the present invention to provide an ECG recorder which records, in analog, the ECG signals received from a patient, and simultaneously analyzes and digitally records analysis information.

It is further an object of the present invention to provide an ECG recorder which performs real-time analysis of ECG signals and digitally records summary information related to predetermined data collection time periods.

It is also an object of the present invention to provide an ECG recorder which performs real-time analysis of ECG signals from a patient and digitally compiles and records an end of monitoring period summary of pertinent information which can be retrieved during rewind of the tape.

It is another object of the present invention to provide an ECG recorder for performing real-time analysis of individual heartbeats and digitally tagging each beat with a particular morphology-type as determined by a real-time analysis of each beat, including analysis and morphology typing of heart beats in response to a pacemaker signal.

It is another object of the present invention to provide an ECG recorder which is capable of analysis of the ST segment of ECG waveforms and recordation of summary ST depression and elevation information.

It is another object of the present invention to provide an ECG recorder which is capable of choosing particular ECG waveforms for high accuracy digital recording thereof for analysis purposes.

It is another object of the present invention to provide an ECG recorder which is capable of arranging digital data for recording onto a plurality of tracks of a recording tape in the manner which improves efficiency and accuracy of data transfer to the recorder tape.

It is further an object of the present invention to provide an ECG recorder which is capable of receiving analog signals from a plurality of input channels and automatically selecting a limited number input channels for output of analog data onto the recorder tape based on desired channel signal characteristics such as signal strength and ECG wave amplitude characteristics.

It is another object of the present invention to provide an ECG recorder which includes an operator or patient actuatable event marker which performs the dual function of controlling setup and initialization phases of recorder operation and signalling the occurrence of a patient event during the monitoring phase of operation.

It is a further object of the present invention to provide an ECG recorder which is capable of self-calibration at the beginning of a sampling period prior to accepting and analyzing ECG data from the patient.

These and other objects of the present invention are realized in a preferred embodiment of an ECG recorder which is preferably a cassette recorder designed to be worn by an ambulatory patient for a predetermined time period, usually between 2 and 24 hours. The recorder amplifies electrical activity of the heart and records the wave forms on magnetic tape for subsequent analysis by a scanner, while simultaneously performing its own internal real-time analyses.

The recorder is attached to the patient through 5-lead or 7-lead electrical connections which are attached at various points on the patient's chest by electrodes, and is then carried by the patient continuously over the monitoring period, such as 24 hours, and receives ECG signals from the electrodes which it records onto the tape and which are also sent to a built-in microcontroller for digital real-time analysis and processing.

Because the recorder provides analog information and digital real-time analysis information of ECG waveforms simultaneously onto a cassette tape for downloading into a scanner, the recording, including all analog waveforms and digital analysis data thereon, is permanently stored for review and/or editing at any time after the completion of the monitoring period.

The recorder of the present invention preferably records four channels of information, including two channels of continuously recorded analog ECG wave forms and two channels of real-time digital analysis of the ECG signals, along with analysis reports including heart rate, rhythm, ST levels, paced beats, and summary reports including beat-by-beat and ST trend analysis information. The recorder also includes an internal clock which is recorded along with other processed ECG data which assists in the avoidance of data distortions during playback of the tape by the scanner.

The digital representations of the ECG wave forms received by the recorder are processed by the microcontroller and a beat detect and classification label are assigned for each detected beat based on feature extraction, template matching and cross-correlation of beats detected on both ECG data channels. This information is stored digitally on the tape for each beat and may consist of any one of a predetermined set of morphology types such as: normal QRS, abnormal QRS, learning phase pulses, calibration pulses, pacemaker driven (paced) beats, beats which the pacemaker failed to sense, failure of a proper beat response to a pacemaker signal, etc. ST trend analysis (ST level) data is digitally recorded to the fourth data channel of the tape, along with the time clock and date. Further if desired, an event indicator may also be digitally recordable on the fourth channel. In addition, the microcontroller calculates numerous parameters and records the information at the end of the tape on both digital channels. This recording of the summary data at the end of the tape is encoded in reverse, thereby allowing the information to be retrieved from the tape during rewind thereof by the playback deck of the scanner.

A scanner including a playback deck as identified herein are more fully described in co-pending U.S. Pat. application Ser. No. 790,045, filed Nov. 12, 1991 and now U.S. Pat. No. 5,305,205 entitled "Ambulatory ECG Analysis System", which is incorporated herein by reference.

The recorder of the present invention passes through three main phases of operation during use. The first is the initialization and set up phase of the recorder. In this phase of operation, the recorder ensures that the leads and electrodes are properly functioning, sets the gain for the two channels of ECG signal data. The second phase of recorder operation includes the recording of calibration pulses prior to a short learning period wherein the recorder receives the patient's heartbeats and sets a beat detection threshold based on a "learned" normal beat of the patient.

The third phase of the recorder operation includes the recording of ECG signals and simultaneous analyzes and classification of beats into "normal" "paced" or "abnormal" categories, and ST segment analysis. This phase also includes accumulation and recording of "minute-by-minute", "hour by hour" and "end of period" summary information

BRIEF DESCRIPTION OF THE DRAWINGS

The above noted and other features of the invention will be better understood from the following detailed description of the invention when considered in conjunction with the accompanying drawings, in which.

DETAILED DESCRIPTION OF THE INVENTION

Figure 1A:
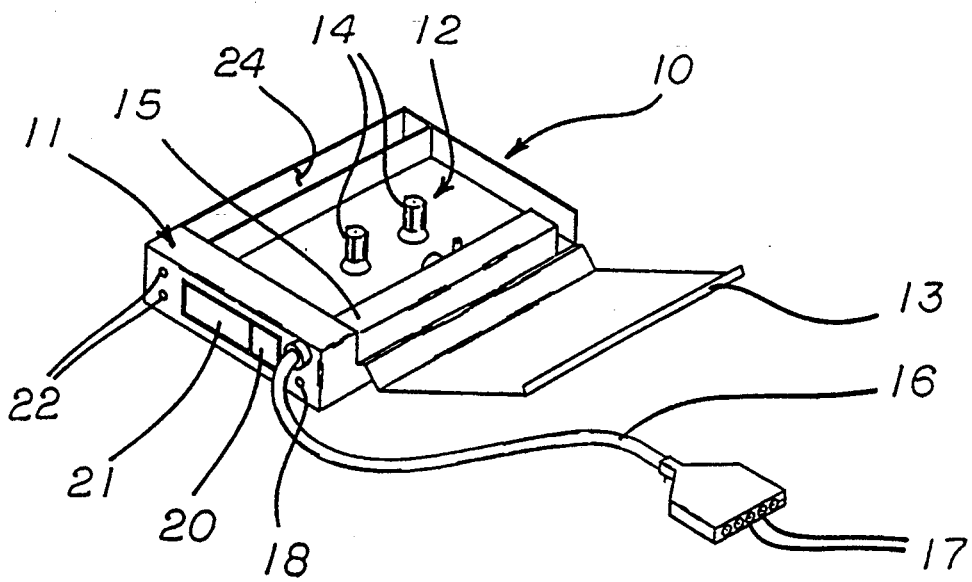
FIG. 1a shows a perspective view of an ambulatory recorder formed in accordance with the principles of the present invention.

As shown in the exemplary drawings for the purposes of illustration, an embodiment of a recorder made in accordance with the principles of the present invention, referred to generally by the reference numeral 10, is provided for ambulatory recording and analysis of ECG wave forms received from a patient.

More specifically, as shown in FIGS. 1(a) and (b), the recorder 10 is preferably formed of a plastic housing 11, such as PC/ABS resin, which includes a cassette compartment 12 therein which is coverable by metal lid 13. The cassette compartment 12 includes cassette hubs 14 for receipt of a standard tape cassette, such as a normal bias, IEC type I, 0–90 cassette tape, and a tape head bar 15 which is rotatable from a first position in which the cassette can be inserted into the cassette compartment 12, to a second position in which the tape head bar 15 is in operable contact with the tape.

The recorder 10 includes a permanently attached electrode cable 16 extending therefrom which has electrode lead inputs 17 located at the remote end thereof. The lead inputs 17 receive electrical leads which extend from electrodes placed in contact with a patient's body to provide electrical input into the recorder 10 corresponding to ECG signals from the patient.

The housing 11 also includes a 3-channel, 4 pin test box jack 18 which allows the test box 19, through test box cable 23, to be attached to the recorder 10. The test box can be connected to an ECG cart and monitor (not shown) through output jacks 25 for electrode placement verification as will be explained below.

An event marker 20 also is located on housing 11. The event marker 20 is used by the medical worker to assist in the set up and initialization of the recorder 10, and later by the patient during the analysis phase of operation for inputting information directly onto the cassette tape. The event marker 20 may also be used for interrupting or aborting the monitoring procedure should it become necessary.

The housing 11 further supports a display 21, preferably an LCD, which displays the operational status of the recorder 10, and a set of timer controls 22, for setting and controlling the operation of the internal clock. A battery compartment 24 is located within the recorder 10 so as to be accessible when lid 13 is in the open position to receive batteries necessary for operation of the recorder 10. The batteries are preferably four, 1.5 volt alkaline (size AA) disposable batteries, which can supply power for a minimum of 25 hours of recorder operation.

The recorder 10 may be placed in a carrying case (not shown) for convenience in attaching it to the patient during use. The carrying case may also include separate compartments, if desired, to store accessories useful with the recorder 10, such as an event diary and recording instrument therefor.

For best tape speed, accuracy, and durability, the recorder 10 is preferably manufactured with a direct gear drive from the motor (not shown) to the capstan, instead of a belt drive as is commonly used. The direct gear drive of the present invention allows the recorder 10 to run at a speed of 1 mm/sec $+/-$ 0.2%, with a stability of greater than 99.5% over long term operation.

The recorder 10 is preferably built without an on/off switch, with the power-on and start up of recorder operations being initiated as soon as batteries are inserted into the battery compartment 24. The recorder 10 will automatically switch off at the end of a preprogrammed monitoring period.

If desired, an accessory kit may be included with the recorder 10 which can conveniently contain all necessary materials for preparing a patient for ambulatory recording of ECG signal data. Each kit may contain any combination of: a cassette tape, such as a TDK D-90; five (or seven) disposable Holter electrodes, including the necessary tape and solid electrode gel for their proper attachment to the patient; four 1.5 volt AA alkaline batteries to power the recorder 10; one patient diary for recording information corresponding to the patient's physiological condition at the time the patient event marker is pushed; and, a razor, alcohol prep-pads, adhesive strips, etc. for preparing electrode sites on the patient's chest. Other accessories such as operator's manuals, five or seven lead cables, head cleaning cassettes, shoulder straps, belts, recorder cases, 1.5 volt lithium batteries, etc., may also be included as part of the kit or provided separately as needed.

Figure 2:
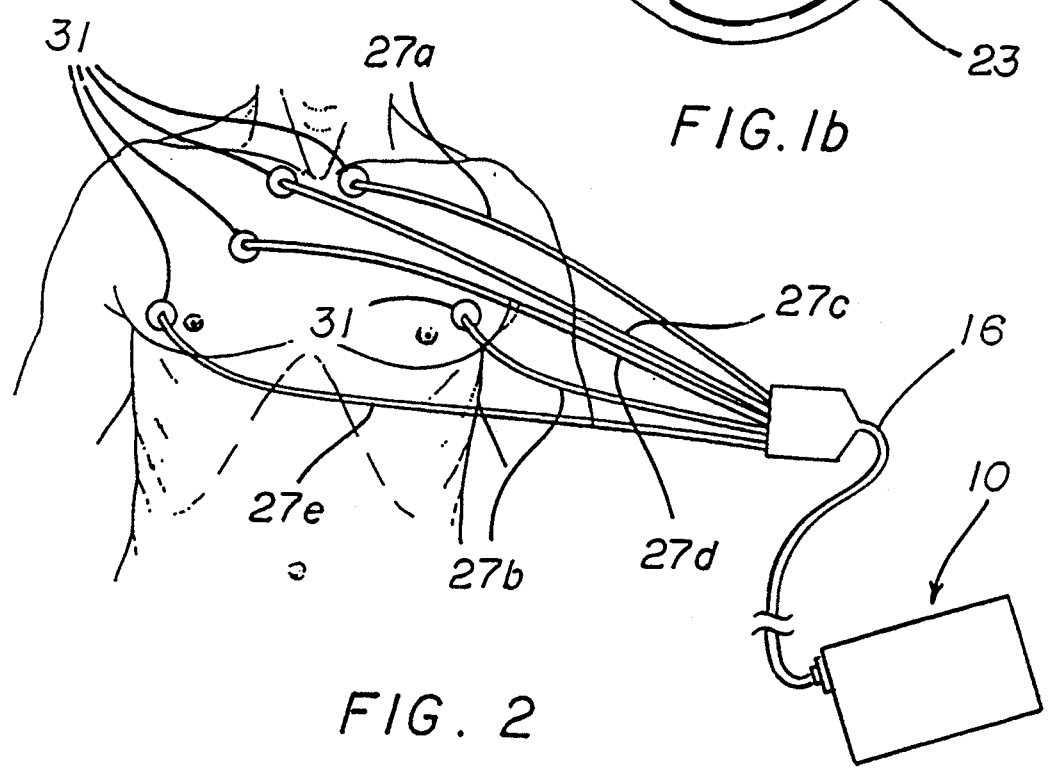
FIG. 2 is a schematic view of a patient showing the recorder of the present invention operationally attached to the patient's chest.

FIG. 2 shows the recorder 10 as configured for use in ambulatory ECG monitoring of a patient. For the recorder 10 to properly receive ECG signals from the patient, at least five, and optionally seven, electrodes 31 must be attached to the patient and to the recorder 10 through leads 27 (leads 27 (a–e) in the case of five electrodes 31 or leads 27 (a–g) in the case of seven electrodes). For example, electrodes 27a and 27b corresponding to a first channel of ambulatory ECG input data may be applied to the patient's chest at the right manubrium (RA) and the left center of the chest over the sixth rib (CMV5) respectively. Electrodes 27c and d, corresponding to a second channel of ECG input data can be attached to the left manubrium (LA), and the right sternum over the fifth rib, respectively. A final lead 27e used as a ground may be attached to the right center of the chest over the sixth rib. Further, if desired, two more electrodes (not shown) corresponding to a third channel of ECG input data may be attached to the patient at locations preferred by the physician.

Figure 3:
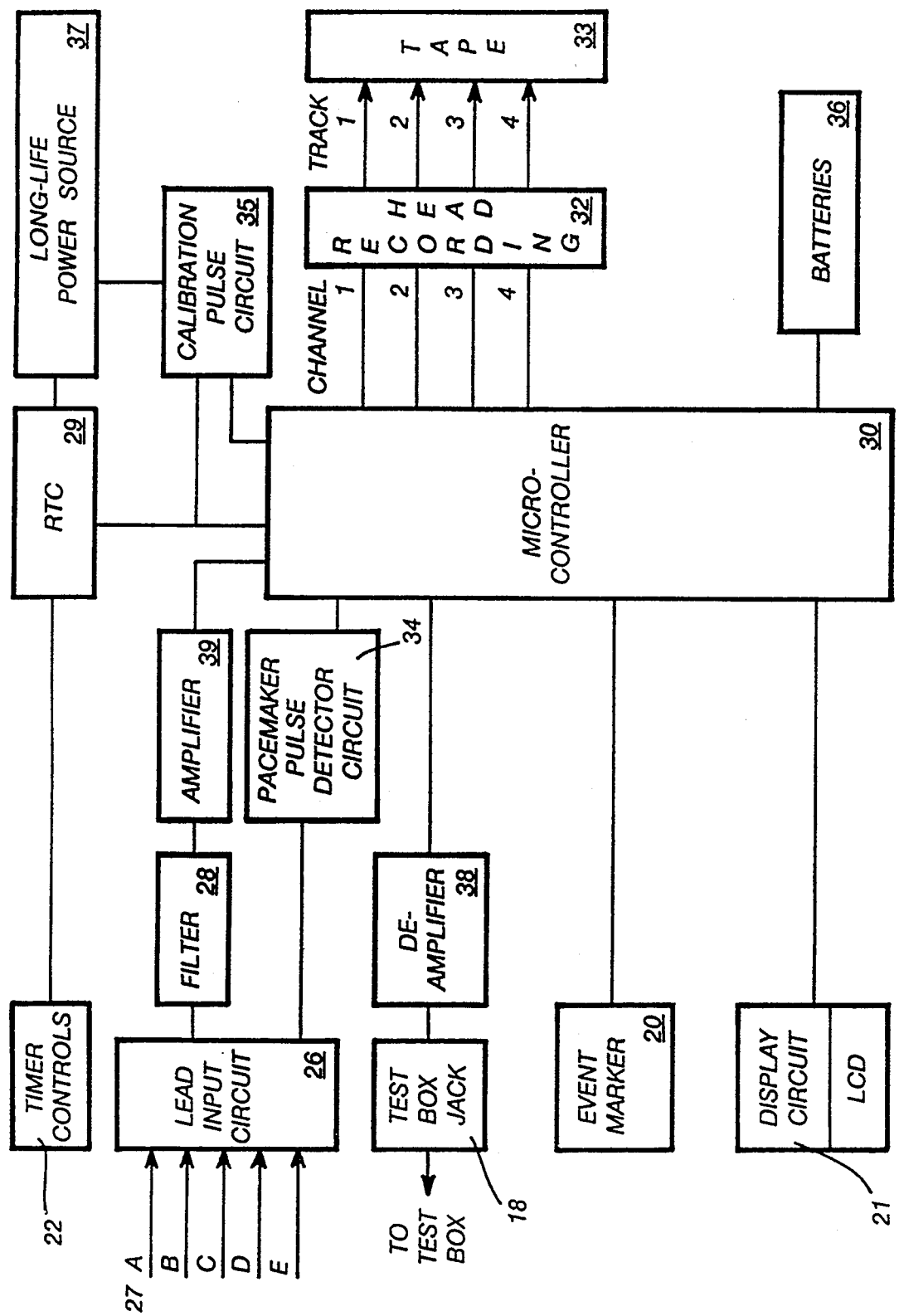
FIG. 3 is a block diagram of the ambulatory recorder formed in accordance with principles of the present invention.

As best shown in the block diagram of FIG. 3, the leads 27 are connected into the recorder 10 which has a frequency response for ECG wave forms of 0.05 Hz to 100 Hz, with a signal range of +/− 4 mV at an input impedance of at least 3 Megohms. The ECG signals pass into lead input jack 26, through a muscle artifact filter 28 and amplifier 25, and into a microcontroller 30.

Figure 1B:
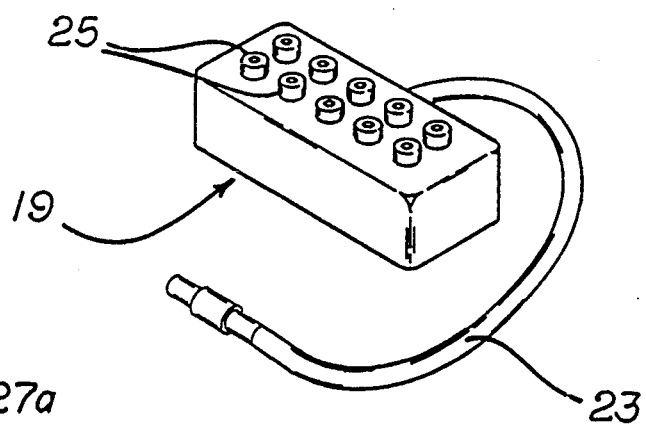
FIG. 1b shows a perspective view of a test box for optional use with the recorder of the present invention.

To verify that the electrodes have been properly placed and leads have been properly connected to allow ECG signals to be received by the microcontroller 30, the test box 19 may include a test box jack 18. An ECG unit (not shown) which preferably includes a monitor or a chart recorder, can be connected through test box jacks 25 (see FIG. 1(b)) to the test box 19. ECG signals from leads 27 pass into the recorder 10 through the lead input 26, and through filters 28 and amplifier 39 into the microcontroller 30, when they are routed through de-amplifier 38 to test box jack 18. The signals then pass out the test box jack 18 and through the test box 19 to the ECG unit where the quality of the ECG signals being received by the recorder 10 can be monitored by the medical worker. Adjustments can then be made to the electrodes to maximize the reception quality of the ECG waveforms.

The reference timing for the recorder 10 is provided by a 32 Hz real-time clock (RTC) 29, such as a model MC68HC68T1, which inputs directly into the microcontroller 30. Timer controls 22 located on the housing 11 of recorder 10 allow the time and date of the RTC 29 to be set by the medical worker prior to use. The display 21, preferably a liquid crystal (LCD), can display the current time of day throughout an entire monitoring period, along with intermitted displays of coded messages indicating the status of operation of the recorder 10. The display 21 also is used to assist the medical worker with status information related to set-up, calibration and initialization operations as will be explained in detail below.

A long-life power source 37, (such as a lithium battery), which is separate from the batteries 36 used to operate the recording hardware, is internally mounted within recorder 10 and controls the memory of the RTC 29, along with the power used by the microcontroller 30 during analysis operations. The power source 37 also maintains power to the microcontroller default memory on a continuous basis.

The patient event marker 20 inputs directly into the microcontroller 30 and serves several functions. Most importantly, the patient event marker 20 allows iteration with the recorder 10 by the patient each time a significant event occurs (e.g., a significant physical sensation experienced by the patient during the monitoring period) to mark the cassette tape 33 at that point in the recording for quick reference during analysis. When pressed and released within five seconds, the patient event marker 20 prompts the microcontroller 30 that a patient event has taken place. In response, the microcontroller 30 marks the tape 33 and records the time, and then stores all data related to the event for later processing. The event marker 20 is also used by the medical worker during initialization and set up of the recorder 10 in order to activate or deactivate various set-up and initialization functions. If desired, the patient event marker 20 can also be used to abort recording during the recorder 10 operation. To abort the recorder operation, the patient event marker 20 is pressed and held for at least five seconds, at which time the recorder operation abort command is acknowledged and an abort message "rEp" appears on the display 21 and a recorder termination sequence is initiated.

The microcontroller 30 is connected for output to the recording head 32 for recording four channels of data at a preferred rate of 256 samples per second per channel onto four tracks of the cassette tape 33. Channels 1 and 2 of data are sent to Tracks 1 and 2 respectively of the tape 33, and contain analog data corresponding to ECG signals received through electrodes and leads 27. Track 3 of the tape 33 receives digital data including beat detection and classification (beat morphology) data, analyzed minute-by-minute information data, and end of monitoring period summary data, each of which will be explained in detail below. Track 4 also receives digital information including minute-by-minute analysis information and end of monitoring period summary information, and further receives and records the time from the RTC 29.

All tasks performed by the recorder 10 are coordinated and controlled by the microcontroller 30. The microcontroller 30 also controls the above-identified peripheral devices including the display 21, the tape drive (not shown) and the operational characteristics of the event marker 20. An example of a microcontroller which is acceptable for use with the present invention is a Motorola 68HC11A0 microcontroller which operates at a speed of 2 MHz and can access 32 K bytes of ROM and 32 K bytes of RAM memory.

A pacer pulse detector circuit 34 is also included in the recorder 10 to detect a spike pulse generated by a pacemaker (generally within a 75 Hz to 1.5 K Hz bandwidth) and to signal the microcontroller 30 of the occurrence of the spike pulse for purposes of assigning a proper beat morphology to the pacemaker assisted heart beat.

Figure 4:
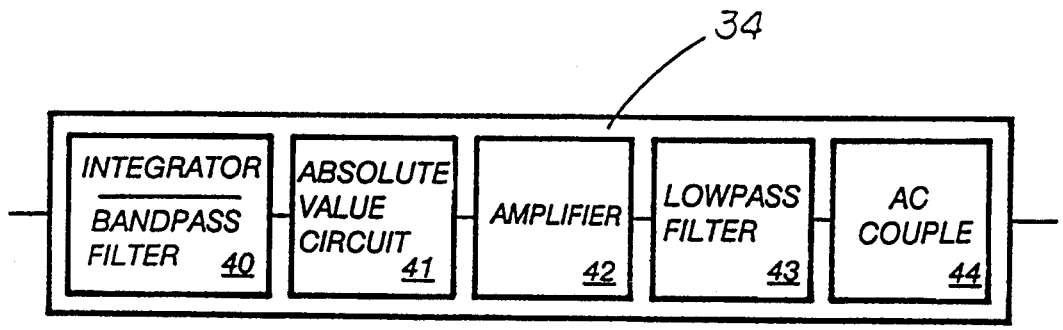
FIG. 4 is a block diagram of the preferred pacemaker spike pulse detector circuit of the present invention.

As shown in FIG. 4 a pacemaker signal of the proper bandwidth received through lead input jack circuit 26 is sent to the pacer pulse detector 34 and Connected to the input of the integrator 40 which is used as a bandpass filter. The output of the integrator 40 is input into the absolute value circuit 41. The signal at the output terminal of the absolute value circuit 41 is a derivative of the amplitude of the spike detect signal which was sent to the pacer pulse detector 34. This signal is then passed through amplifier 42 and matched with a predetermined voltage range (preferably between 50 mv and 5 v) to be identified as a detection of a pacemaker spike pulse. If the predetermined voltage criteria is met, the signal is identified as a pacer spike and passed through the low pass filter 43 and AC couple 44 and sent to the microcontroller 30 where an "interrupt" is generated to allow identification of the patient's next heart beat in the manner as will be explained below.

GENERAL OPERATION

The recorder 10 of the present invention is sized and designed to be easily transportable by an ambulatory patient while recording the patient's ECG signals. Since the present invention collects ECG signals over an extended monitoring period, often 24 hours in duration, a medical worker can receive useful information about the patient's heart activity during normal daily exertions. Long term monitoring significantly increases the medical worker's ability to diagnose cardiovascular problems compared to prior art non-ambulatory or short period ECG monitoring. Further, by close analyzes of information input by the patient through the patient event marker 20 and related diary entries, the medical worker can focus on particular abnormalities which may have occurred over the recording period.

As an added analytic and diagnosis tool, the recorder 10 of the present invention summarizes ECG information on a minute-by-minute basis, an hour by hour basis, and an end-of-period basis, and records the summaries onto the cassette tape. The end-of-period summary is recorded onto the cassette in such a manner (explained in detail below) that it can be downloaded and printed for the medical worker's review during the initial rewind of the cassette, even before playback of the remaining collected information.

Figure 5:
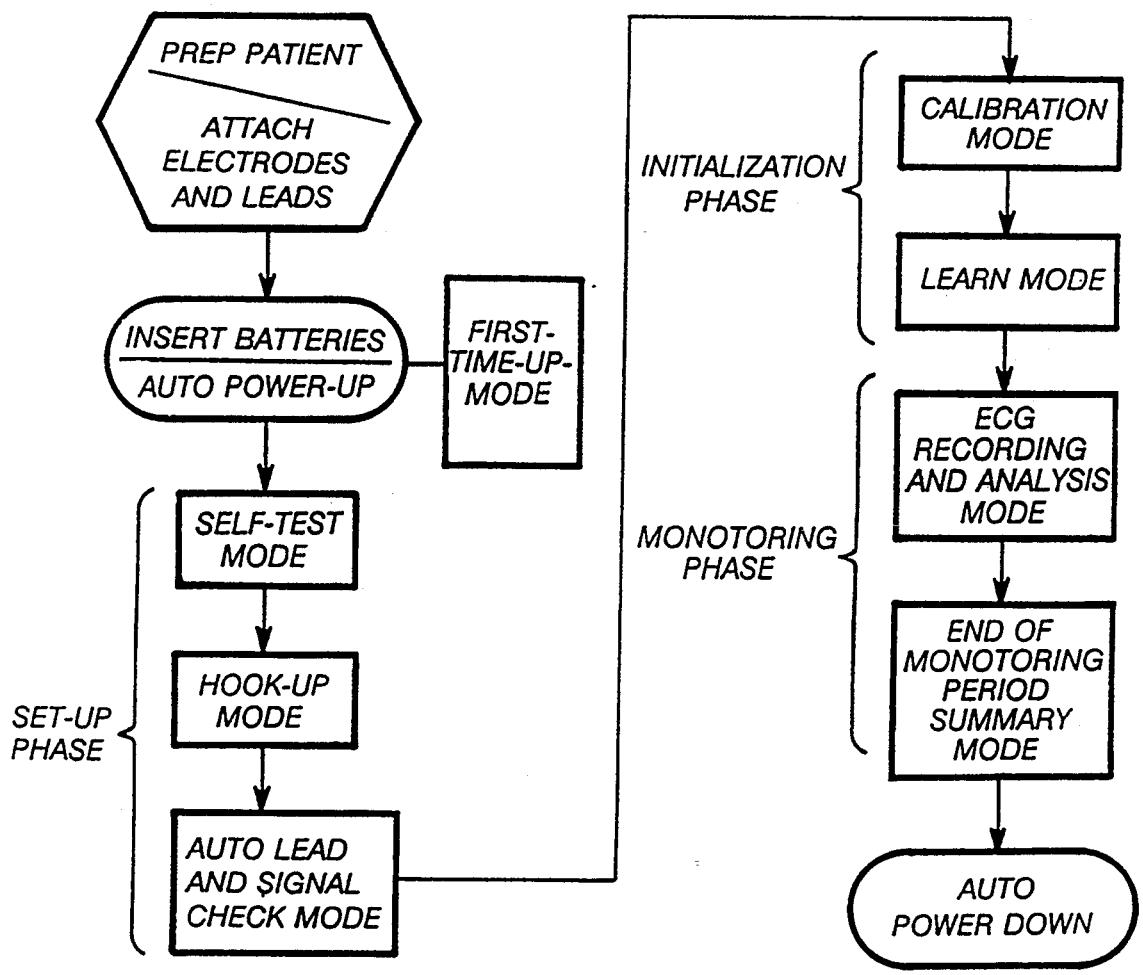
FIG. 5 is a flow chart of the preferred procedure of operation of the present invention.

As shown in FIG. 5, the general operation of the recorder 10 of the present invention can best be described when broken down into three distinct phases of operation. The first phase is the Set-Up phase, which prepares the recorder 10 for reception and simultaneous analysis of ECG data. The Set-Up phase includes automated electrical systems diagnostics and ECG signal strength evaluations. The second phase is the Initialization phase, in which the recorder 10 is calibrated and operated on the patient to form an initial template of the patient's "normal" heart beat. The third phase is the Monitoring Phase, in which ECG signals from the patient are recorded on the tape 33 in analog, along with simultaneous digital recording of analysis information. The analysis information is organized to generate segmented summaries of analysis results, and an end-of-monitoring period summary which includes information collected during the entire Monitoring phase.

Prior to the Set-Up phase of the recorder 10, the electrodes and leads are attached to the patient, preferably in the manner as described above, and the leads are attached through to lead inputs 17, through the electrode cable 16 to the recorder 10. A cassette 33 (preferably new) is then inserted into the recorder 10, and power is supplied to the recorder 10 (preferably by four new 1.5 V AA alkaline batteries). On installation of the batteries, the recorder 10 automatically powers up and begins the Set-Up phase of its operation.

As a result of power up of the recorder 10, the microcontroller 30 determines the status of the RTC 29. If the recorder 10 has never been powered up, the RTC 29 will be found in the "first time up" mode, and the microcontroller 30 will initialize operation of the RTC 29 and the display 21 to allow the medical worker to set the RTC 29 to the proper time and date with the timer controls 22. Also during the "first time up" mode, the microcontroller 30 sets the analog data channels, which receives the ECG signals, to the preferred sampling rate of 256 Hz.

Set-Up Phase

In the Set-Up phase, specific registers and ports in the microcontroller 30 are configured to communicate with the peripheral devices (e.g., RTC 29, display 21, event marker 20, etc.) and to enable a pair of electronic "interrupts". The first interrupt is a "period interrupt" which is in the form of a periodic electrical pulse which provides the source of all timing in the microcontroller 30. The periodic interrupt pulse is provided by the RTC 29, preferably at a rate of 256 Hz (i.e. 3.90625 ms) and is input to the microcontroller 30. The falling edge of the period pulse from the RTC 29 is recognized by the microcontroller 30 to generate the initiation of each periodic interrupt period.

The second interrupt is a "pacer detect interrupt", and is generated when the pacer pulse detection circuit 34 detects a pacer pulse from a pacemaker and reports it to the microcontroller 30. This interrupt is dedicated to the detection of electrical pacer pulses applied to the heart by a pace maker should one be in use by the patient, and operates to allow the microcontroller 30 to identify subsequent heart activity as corresponding to either a heart beat in proper response to the pacer pulse, a failure of the heart to respond properly to the pacer pulse, or a failure of the pacemaker to sense that a proper heart beat had occurred without the need for the pacer pulse.

If the recorder 10 has previously been operated, power up does not bring the recorder 10 up to the "first time up" mode. Instead, the recorder 10 moves directly to the "self-test" mode and the display 21 displays the present time and date for validation by the medical worker. If the time or date is invalid, the medical worker can reset the RTC 29 using the timer controls 22. In either event, the microcontroller 30 causes the RCT 29 to display the time, and then waits approximately 20 seconds for the medical worker to either reset the time and date, or validate the time and date as shown on the display 21. Validation of the time and date is assumed if the medical worker fails to operate the timer controls 22 within the 20 second period.

At the expiration of the 20 second period, the recorder 10 moves into the "hook-up" mode in which the patient's ECG waveform signal size and quality, as being picked up by the recorder 10, can be visually checked. Visual review of the signals is accomplished by connection of a standard 12 lead ECG unit (not shown) to the recorder 10, which includes either a chart recorder or a scope. This is done by connecting the test box 19 to the recorder 10 by inserting test box cable 23 into the test box jack 18. The 12 leads from the standard ECG unit are then inserted into the test box ports 25. The ECG signals then pass from the patient through the electrode cable 16, through the lead input deck 26 and filter 28, and out the test box jack 18 through the test box 19 to the standard ECG unit where they are recorded on a graph or displayed on a monitor. If the received ECG signals are not to the medical worker's satisfaction, the electrodes can be moved or adjusted on the patient's body to improve the waveform shape or quality.

At the beginning of the above described "hook-up" mode, the tape 33 begins to move and the recorder 10 begins to record the ECG signals onto the first two tracks (Tracks 1 and 2) of the tape 33. However, no analysis is performed during this mode by the recorder 10. If no visual check of the signal quality is desired by the medical worker, the "hook-up" mode can be completely bypassed by merely pressing the event marker 20.

After the "hook-up" mode has been completed (or bypassed), the tape 33 stops and the recorder 10 moves into the "lead and signal check" mode. In the present preferred embodiment of the invention, lead checking is accomplished by passing a 2 Volt peak-to-peak square wave from the microcontroller 30 through each lead wire. Lead checking requires approximately 5 seconds per lead, 3 seconds being used for monitoring each lead, and 2 seconds for displaying its status in display 21. For example, if the first lead 27(a) is being checked, lead display 21 will read "C L1", meaning "checking lead No. 1". If the lead 27a is properly connected, the display 21 will flash "C L1 YES" and then proceed immediately to check the next lead 27b. If the lead 27a is not adequately connected, the display 20 may flash "C L1 NO" and continuously sound an audible alarm for a period of 1 minute or until the lead 27a is adjusted for adequate connection.

Each lead 27 is checked in a similar manner, however, if a failure in any one of the leads 27 is found, the lead monitoring and auto-check process stops and does not proceed to the next lead 27 or the next phase of operation until the previous lead 27 is either fixed, or the failure is bypassed by the medical worker by pressing the event marker 20. If the medical worker prefers to bypass any lead check, and therefore presses the event marker 20 at the proper time, the display 21 will momentarily read "ESC" and the recorder 10 will move on to check the next lead. If desired, all lead checks may be bypassed by the medical worker.

Once each lead had been checked, the recorder 10 again pauses, preferably for a period of 6 seconds, before beginning the signal checking portion of the "lead and signal check" mode. This delay is required for ECG signal stabilization after completion of the lead checking. During this time, the display 20 will read "PAUSE" to indicate the transition from lead checking to signal checking.

During signal checking, data from all three analog channels (two if only five leads are used instead of seven) are analyzed for a period of 12 seconds to set the gains for each channel. Gain for each channel is set to a 0.2 v amplitude pulse generated from the microcontroller 30. While each gain is being set, the display 21 will read "ECG GN". The total time required for setting the gains on each channel is approximately 30 seconds. However, if the recorder 10 finds that no signal is received on a particular channel, it will stop and the display 21 will read "NO CH X". Likewise, should the gain be extraordinarily low on a particular channel, the recorder 10 will stop and the display 21 will read "CH X LO". In either instance, the medical worker must adjust the leads to improve the signal thereby, or otherwise advance the program by pressing event marker 20. Once the gain has been set for all channels, the display 21 displays each channel individually with its adjusted gain. For example, the display 20 may read "CH1 G2" meaning channel 1, gain setting 2, and similarly for each channel.

Also during signal checking, the recorder 10 picks two of the three ECG signal data channels for analysis, and assigns one channel to be recorded on Track 1 of the tape 33 and the other to be recorded on Track 2. (This step of course is only necessary if 3 channels of ECG signals are being input into the recorder 10 due to the presence of seven leads instead of five.) If data quality on any channel becomes poor at any time during the monitoring period, i.e., the data amplitude falls below an acceptable level, the recorder 10 automatically goes back to the lead checking mode, rechecks the leads and signals, and re-chooses the best two channels for recording.

Once the lead checking is complete, the recorder 10 proceeds to the Initialization Phase of its operation.

Initialization Phase

It should be noted that information recorded to the tape 33 prior to the Initialization phase is not necessarily used in the recorder 10 during the Analysis Phase, nor when the tape 33 is downloaded into a scanner after the recording period is complete. However, from the very beginning of the Initialization Phase, the tape 33 is continuously recording information received from the microcontroller 30 until the recorder 10 automatically powers down at the end of a completed or aborted monitoring period.

During the first approximately six minutes of the Initialization Phase, the recorder 10 is in the "calibration" mode. During calibration, pre-programmed calibration pulses are generated by the calibration pulse circuitry 35 and sent to the tape 33 to be recorded. An example of a calibration pulse which may be used would be a 1 Hz, 1 mV pulse, with logic zero for 875 ms. and logic 1 for 125 ms (i.e., a 1 second wide 1 mV pulse with a ⅛ second data cycle), however any similar pulse and pulse logic may be used. The calibration pulses remain unused and unanalyzed on the tape 33 until it is removed from the recorder and inserted into the playback deck of the scanner after the completion of the monitoring period, at which time the calibration pulses are used by the playback deck of the scanner for self calibration.

The calibration pulses are recorded onto Track 1 and Track 2 of the tape 33 in analog form in the same manner that the patient's own ECG signals are to be recorded. However, during recordation of the calibration pulses, the patient's own ECG signals received by the recorder 10 are ignored, and only the calibration pulses are recorded onto the tape 33.

While the recorder 10 remains in the "calibration" mode, the medical worker chooses the desired recording period length by pressing the event marker 20 to cycle the display 21 through the various predetermined monitoring period lengths. For example, the recorder 10 may be preset to several monitoring period lengths, such as 24 hours, 23 hours, 12 hours, or 2 hours. The medical worker merely chooses which monitoring period length desired and cycles the display 21 until the proper time is shown. While awaiting a decision by the medical worker, the display 21 will read "CAL XX H" where "X" represents each one of the preset monitoring period lengths (in hours) which the medical worker can choose from as the display 21 is cycled.

Once the "calibration" mode is completed and the medical worker has chose a monitoring period length by pressing the event marker 20 until the desired time period is displayed, the recorder 10 moves immediately to the "learn" mode in which the recorder 10 "learns" to: i) detect a beat and identify it as such, and ii) classify the beat as having a particular morphology. The "learn" mode extends for an approximately four minute duration, with annotations being output onto the tape 33 every second. The first approximately four seconds of the four minutes are used as a stabilization period to allow the recorder 10 to switch from recording calibration pulses back to recording ECG signals from the patient. The next approximately eight seconds are used to set a beat detection threshold, and the remaining time is used to achieve a steady, stable heart rate and learn a "normal" beat. All beats exceeding the beat detection threshold after the completion of the learn period are then counted and classified as either "normal" (N), "paced" (P), or "abnormal" (V) beats. Annotations corresponding to the detection and classification of each beat are thereafter digitally recorded onto the tape 33 throughout the remainder of the monitoring period in a manner as will be described in more detail below.

As stated above, once the stabilization period is complete, the recorder 10 begins to develop a beat detection threshold which will subsequently be used to determine the presence or absence of a beat. To accomplish this, a single detection function is developed for both selected channels of incoming analog ECG data, with the detection function being a product of the derivatives of the two selected channels. A more detailed description of a preferred beat detection methodology is as follows.

Beat Detection Template

The preferred process for developing and updating the beat detection threshold which is exemplary of the concept of the present invention is as follows.

First, the raw data signal from both channels of incoming ECG data picked for analysis are subjected to median filter averaging which is definable generally by the following function:

1st channel: $x1 = \text{median of } [x(i-12), x(i), x(i+12)]$

2nd channel: $x2 = \text{median of } [x(i-12), x(i), x(i+12)]$ where x1 and x2 are the median values for channel 1 and channel 2 respectively, and x(i) is the raw data value for the respective channel.

The detection function for each channel is created as follows:

1st channel:
$y1(i) = |x1(i - 3) - x1(i + 3)| + |x1(i - 4) - 2x1(i) + x1(i + 4)|$
2nd channel:
$y2(i) = |x2(i - 3) - x2(i + 3)| + |x2(i - 4) - 2x2(i) + x2(i + 4)|$ where x1 and x2 are the median data for the first and second channels as defined above.

The detect functions y1 and y2 are both filtered through a 28 point triangular window to create two "smoother" detect functions y11 and y22. The "smoothing" is achieved as follows:

$y11(i) = 2y11(i - 1) - y11(i - 2) + y1(i) - 2y1(i - 7) + y1(i - 14)$
$y22(i) = 2y22(i - 1) - y22(i - 2) + y2(i) - 2y2(i - 7) + y2(i - 14)$

Finally, y11 and y22 are combined to create the combined detect function y as follows:

$y(i) = y11(i) * y22(i)$

The two largest peaks found by the detection function y(i) during the 8 second detection threshold determination period are averaged to determine an averaged detect function value of y (identified as "y(ave)") which will be used to set the beat detection threshold. The beat detection threshold is set at 6.35% of y(ave), and a beat is confirmed as "detected" if no other peak is indicated within 15 samples of raw data after detection of the peak. The total delay required by the beat detection is 45 samples, ("delay" being defined as the number of samples between actual occurrence of the peak and the "detection" thereof). Each time thereafter that a beat peak is "detected" above the beat detection threshold, the averaged detection function value y (ave) is updated as follows:

$y \text{ (ave)} = A\, y(\text{ave}) + By$

With A preferably being equal to ⅞ and B preferably being equal to ⅛.

Normal Beat Template Generation

Once the threshold is set for beat detection, the recorder 10 proceeds to analyze particular characteristics of the ECG wave forms and compose a template of a "normal" beat. In the preferred embodiment of the invention, there are two main calculations performed for end pointing and quantifying specific ECG wave form characteristics. The first is a "modified power" calculation which estimates the absolute value of the area described by the ECG wave form as measured by the summation of absolute value distances of sample points on the wave form from a precomputed baseline. The second is a "second derivative peak" calculation which finds the absolute value maximum of a second derivative of the wave form. A more detailed description of the modified power and second derivative peak calculations are as follows.

Modified Power Calculation

Prior to performing the modified power calculation, it is necessary to compute an estimate of the baseline value to be used therein. Although a baseline value is set at initialization of the recording, due to electrical noise such as muscle artifact or to a change in signal due to movement of the patient, the baseline must be constantly re-estimated in order to ensure accuracy of calculations performed on the raw ECG data. The baseline estimate is continuously computed from raw data as follows:

if $x(i) > \text{BASELINE}$ then BASELINE = BASELINE + INT FAC
if $x(i) < \text{BASELINE}$ then BASELINE = BASELINE − INT FAC
Base Corr(i) = $x(i) - \text{BASELINE}$ where x(i) is the raw data value for a channel, and INT FAC is a specific predetermined constant value. The Base Corr(i) is the corrected value of the sample at (i) which is used in the modified power calculation. Recalculation of the baseline to develop a baseline corrected value for the raw data sample is performed for every raw data value as it is received by the channel.

Figure 6:
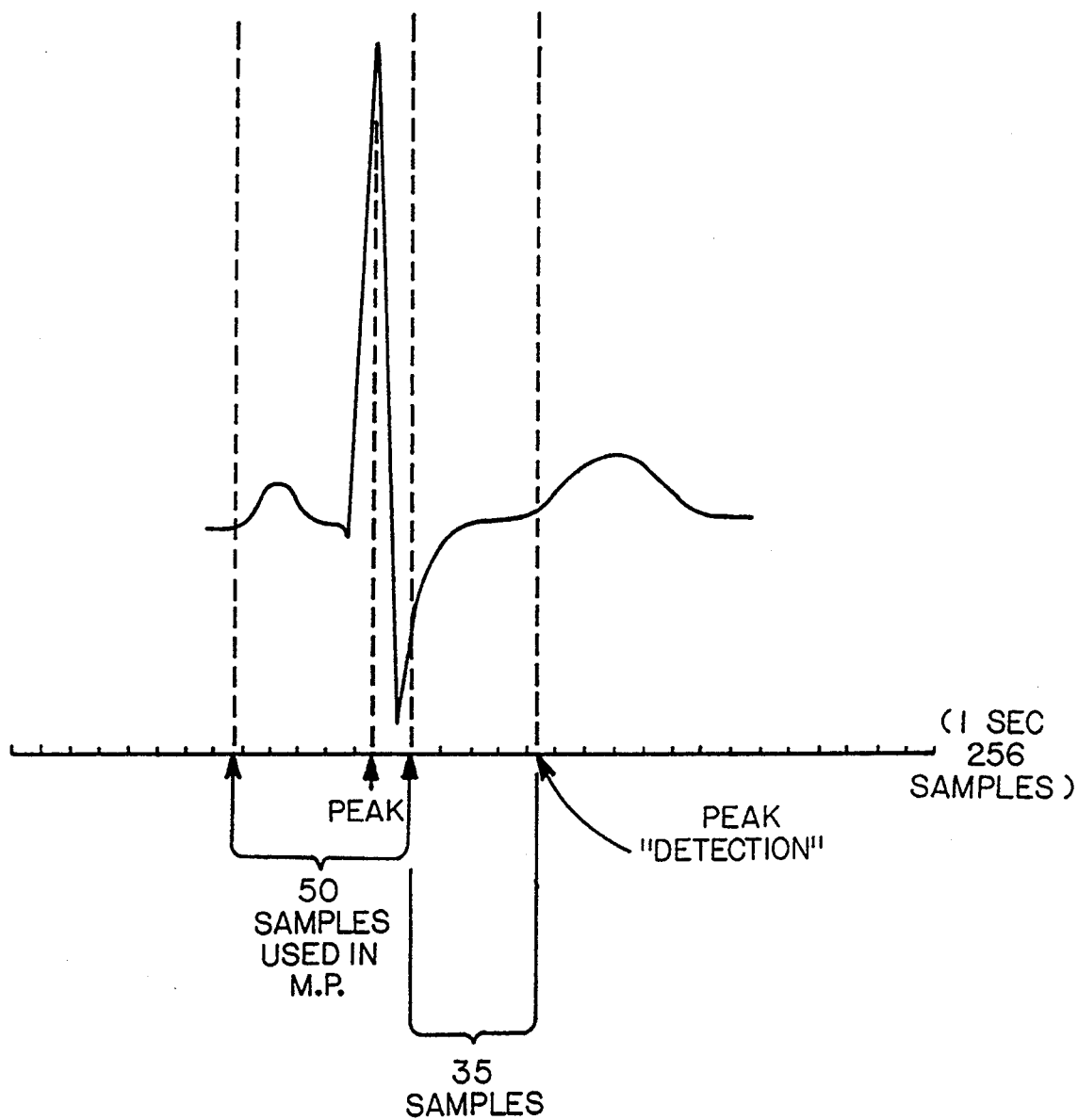
FIG. 6 is a schematic view of an ECG waveform showing the operation of the "Modified Power" algorithm of the present invention.

The modified power (referred to hereinafter as "MP") calculation is a 50 sample absolute value sum of the baseline corrected data (Base Corr(i)) of the major portion of the ECG wave form. As was stated above, a period of time corresponding to approximately 45 samples passes between the occurrence of the peak of the QRS complex and the actual acknowledgement of a beat detection by the recorder 10. Therefore, as shown in FIG. 6, the modified power calculation takes as its 50 samples, the samples between 35 samples immediately prior to the beat detection signal and the 50 samples immediately prior to that. It is intended that choosing the samples in this manner will cause the QRS complex to be included in the MP calculation, while excluding the ST segment of the wave form. The 50 sample sum is computed as follows.

$$\text{Sum} = \sum_{x=1}^{50} |\text{Base Corr}(i - 35 - x)|$$

The MP calculation is performed for each of the incoming ECG analog channels.

Second Derivative Peak Calculation

The second derivative peak (referred to hereinafter as "SDP") is found by searching for an absolute value maximum in a 28 sample window of the second derivative function of the raw data. The second derivative function is computed from raw data samples as follows:

$$\text{Derv2} = x(i-4) - 2x(i) + x(i+4)$$

if (Derv2 > 0) then Derv2 = 0.25Derv2

Figure 7:
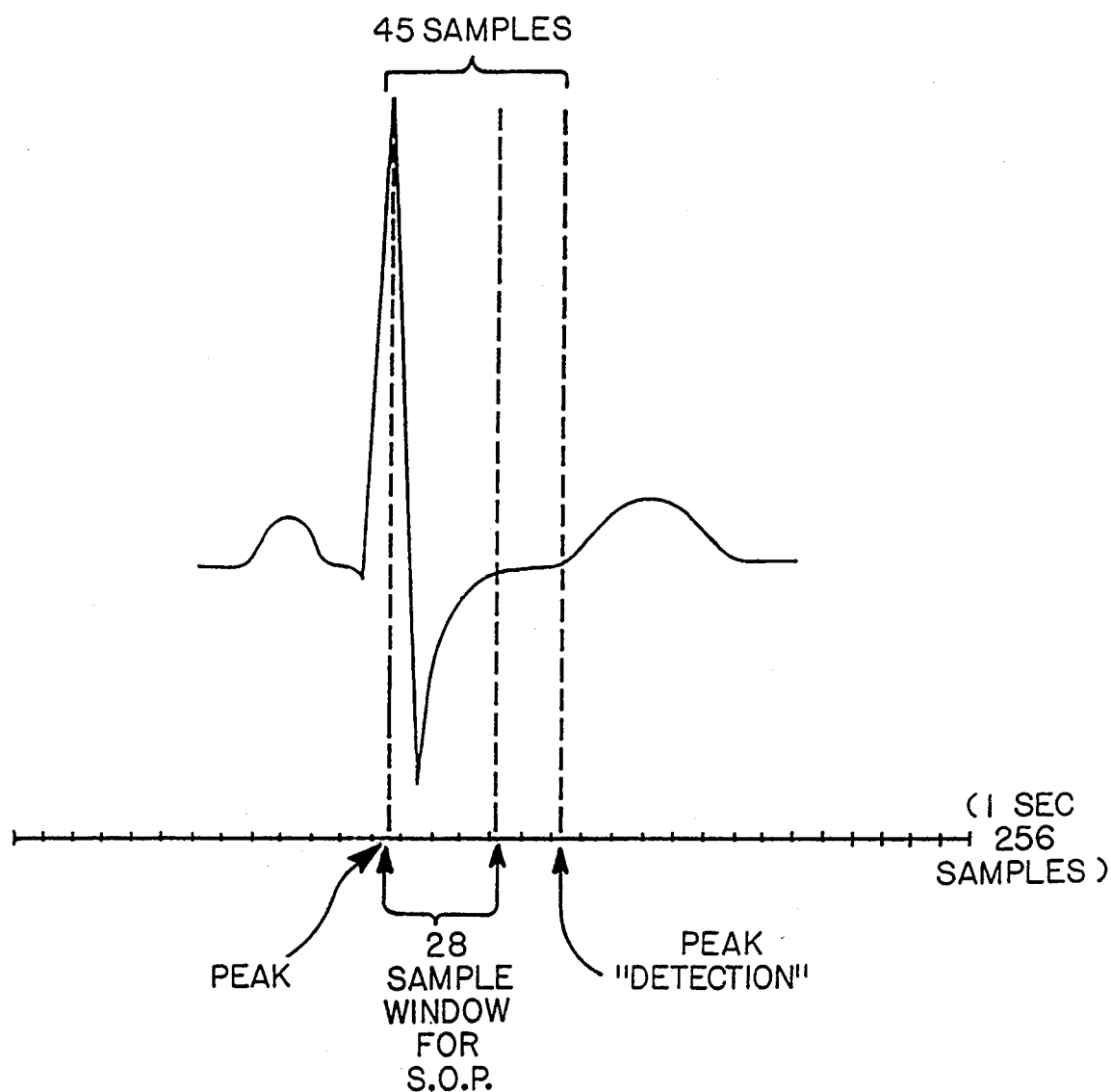
FIG. 7 is a schematic of an ECG waveform showing operation of the "Second Derivative Peak" algorithm of the present invention.
Figure 8:
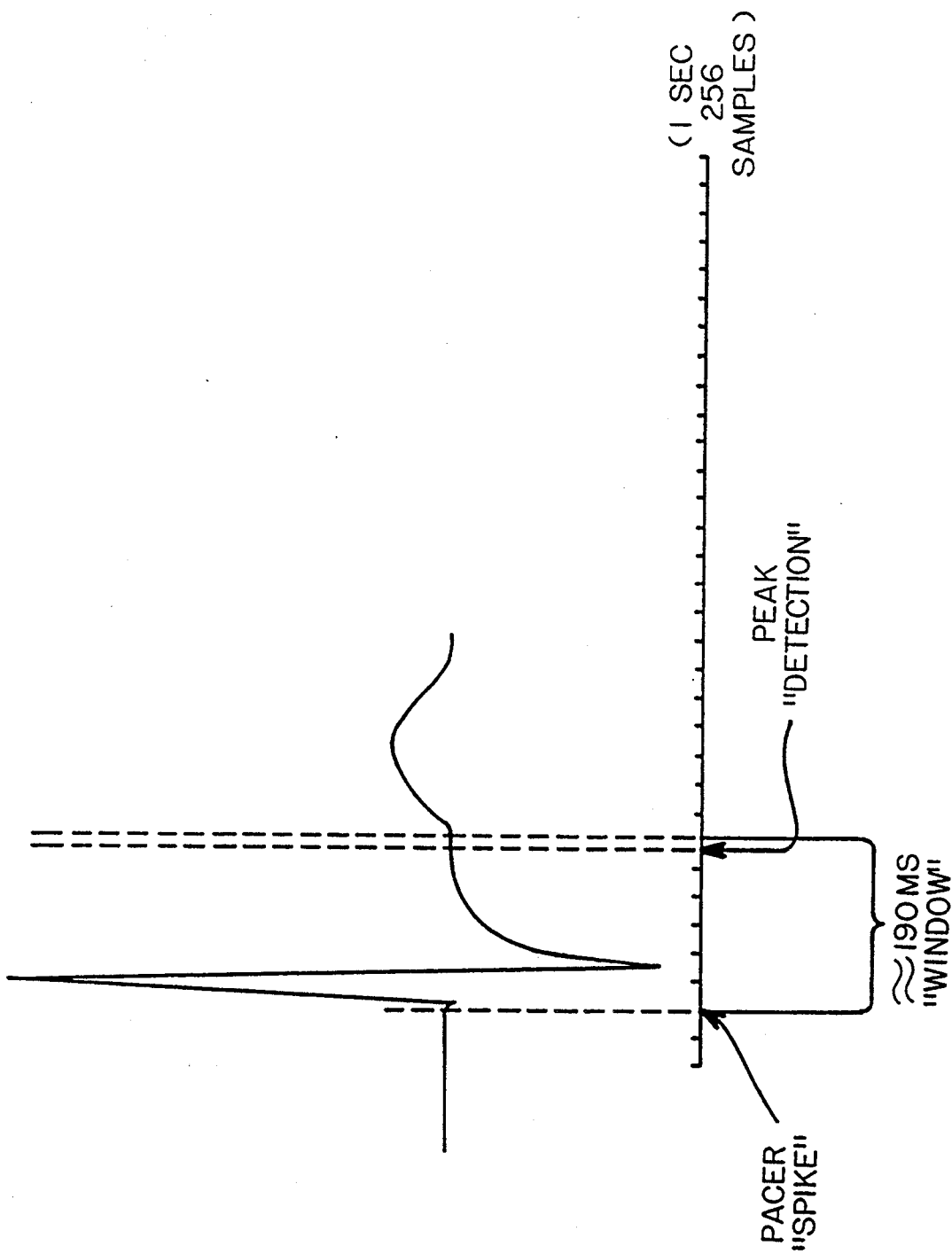
FIG. 8 is a schematic of the preferred method of detection of a pacemaker initiated heartbeat.

As shown in FIG. 7, search process is conducted by backing up 45 samples to get to the peak of the QRS segment and then searching forward in 28 samples to find the second derivative peak.

R-R Interval

The R-R interval is the time interval between R points of adjacent QRS complexes of the ECG waveforms. With each beat detection, a R-R interval is calculated as the number of samples between the current and the previous beat detect. If the current R-R interval is less than 60 samples (corresponding to a heart rate greater than 240 bpm), the beat detect is disregarded along with the R-R interval value. However, if the R-R interval is greater than 500 samples (corresponding to a heart rate less than 30 bpm), only the R-R interval value is disregarded for the purposes of R-R interval averaging. For all valid R-R intervals, an average R-R interval is maintained throughout the system as follows:

Average R-R = (A * Average R-R) + (B * current R-R)

With A and B preferably being ⅞ and ⅛ respectively.

The minimum and maximum R-R for the minute and hour are each computed based on the above average, and the time of day (clock time) associated with the minimum and maximum R-R during the monitoring period are also recorded. The average R-R for the minute is computed by summing all R-Rs for the minute and dividing the sum by the number of R-Rs for that minute. The hour R-R average is similarly computed based on the sum of the minute summations divided by 60. The R-R average for the entire monitoring period is also similarly computed by summing the hour summations and dividing by the total hours. Each minute and hour R-R summary is computed at the end of the minute or hour respectively to which it relates.

After the acquisition of the first "normal" beat, upper and lower limits are set on the MP and SDP features. These limits, in conjunction with prematurity criterion (R-R average) are used to classify beats after the learn period is over.

The MP and SDP limits are preferably a predetermined percentage of the MP and SDP values as they are updated throughout the monitoring period. This percentage is preferably between 80 and 120 percent.

During the entire "learn" mode, the display 20 of the recorder will read "LEARN". Should the recorder 10 fail to learn a template of a normal beat, the display 20 will read "LRN ERR" and the recorder will reset to allow a second attempt to learn the patient's normal beat. Once the normal beat is learned, the display 20 will read "END" indicating the completion of the "learn" mode and of the Initialization phase. It should be noted that after this point, the recorder 10, regardless of errors which may occur during the test, will never again execute the error alarm. If a channel fails after completion of the Initialization phase, instead of activating an alarm, the microprocessor 17 will ignore that channel and monitor the better channel(s) for its analysis. If all channels fail, no beats will be detected, however, the recorder 10 will continue through the entire predetermined monitoring period and complete its operation.

After completion of the initialization phase and throughout the remainder of the monitoring period, the beat detect function for each selected channel is continuously monitored for purposes of ensuring that a good quality ECG signal is being received. To this end, a maximum value calculated by the beat detection function is maintained during the entire analysis. If the beat detect function for any of the two selected channels falls below 25% of its maximum value and remains there for 19.5 seconds (which is equivalent to 5000 samples), a "low amplitude" mode is activated by the recorder 10, and only the channel receiving detection function values closest to its maximum detection function value is used for beat detection. However, the low amplitude channel will continue to be monitored for a short period of time, preferably in the range of 35 to 40 seconds, and reactivated if the detection function value increases and remains within 25% of the maximum value for an extended period. If a low amplitude condition occurs on both channels, the "low amplitude" mode is deactivated, and both channels are again used for beat detection regardless of the beat detection function values received.

Once the Monitoring phase begins, each detected beat is classified as a normal, ventricular, or paced beat as noted above according to the MP, SDP and R-R interval, and their predetermined percentage of variance criterion. If the beat is classified as normal, the beat detection threshold and the MP and the SDP algorithms are updated, preferably in the manner described as follows:

Updated Value = A(old value) + B(new value)

where A is preferably ⅞, and B is preferably ⅛.

Since the beat classification process is time consuming (i.e., it represents a significant computational load on the microcontroller 30), the entire beat classification process, including updating of the beat detection threshold, is spread out to expand over three periodic interrupts in order to sufficiently distribute the calculation process.

Paced Beat Analysis

Figure 9:
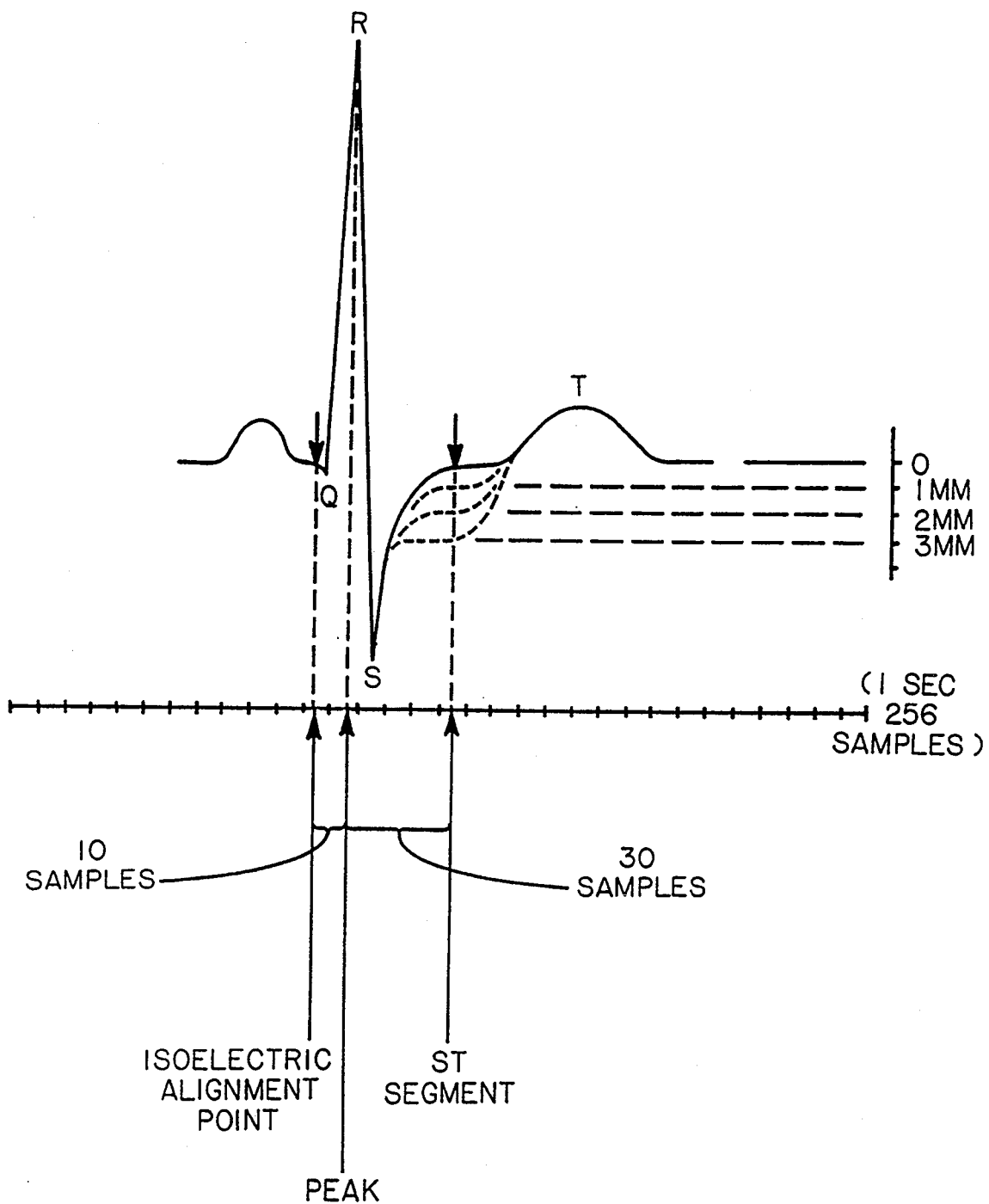
FIG. 9 is a schematic of an ECG waveform showing the preferred method of ST depression level measurement.

If the patient has been fitted with a heart pacemaker device, the recorder 10 of the present invention can sense the emission of a signal therefrom (hereinafter referred to as a pacer "spike") which is intended to initiate a heart contraction. As shown in FIG. 9, sensing of a spike by the recorder 10 triggers the second enabled interrupt, identified above as the pacer interrupt. When the pacer interrupt is acknowledged by the microcontroller 30, a "window" of a fixed period of time, preferably approximately 190 ms. (approximately 48 samples), is monitored by the microcontroller 30 for the detection of the patient's next heart beat. If a beat is detected in this window, it is classified as a "paced beat" meaning the heart properly responded to the pacemaker spike. If no beat occurs in the window, the event is classified as a "non-capture", meaning that the heart failed to respond properly to the pacer spike.

At times a pacemaker may malfunction, due to a loose connection or other similar problem, and the pacer may initiate a pacer spike to trigger a heart beat when a spike was not actually necessary. For example, if a pacemaker fails to properly receive signals from the heart informing it that the heart is beating properly (such as may be the case if a pacemaker sensor wire is faulty) the pacemaker may assume that a spike is needed to generate a heart beat. A spike pulse would then be initiated by the pacemaker even though the heart was beating properly.

The recorder 10 of the present invention can identify this situation, thus aiding the diagnoses of a faulty pacemaker. If a beat is detected, and subsequently a pacer spike is sensed within less than approximately 180 ms. after detection of the beat, the event is labelled and marked by the recorder 10 by an appropriate morphology tag and recorded to the tape 33. This type of occurrence is commonly referred to as a "failure to sense" meaning the pacemaker failed to sense the properly occurring beat and inappropriately initiated a pacer spike. An awareness of regular occurrences of "failures to sense" is helpful to the medical worker in diagnosing pacemaker malfunction.

A final step in beat classification occurs once a beat has been classified and the detection threshold, along with the MP and SDP upper and lower limits, are updated. Each beat which has been classified as normal (either strictly normal or normal SVE) is retrieved in the next periodic interrupt cycle and an ST trend analysis is performed thereon. The details of the ST trend analysis are as follows.

ST Trend Analysis

Each normal heart beat generates a beat wave, such as shown in FIG. 9, which is traditionally broken down into sections identified as PQRS and T. It is important for the medical worker to be able to monitor the level of the ST segment of the heart beat signal since its shape and amplitude have been found to be directly correlated with the amount of oxygen being received by the patient's heart. A heart receiving insufficient oxygen experiences a very predictable anomaly in the ST segment of the waveform called "ST Depression". The name relates to the "depressed" shape of the ST segment of the ECG waveform during periods of insufficient heart oxygenation.

The ST segment of an average patient's ECG wave form is normally located at the same level (i.e., has the same amplitude) as the beginning of the beat (just prior to the Q portion). This is generally referred to as the "isoelectric alignment" of the ST segment with the beginning of the beat. However, if the ST segment becomes depressed, i.e., falls below its normal position, as shown in dashed lines in FIG. 9, it is a reflection of the electrical phenomena caused by inadequate oxygenation of the heart accompanied by a build up of lactic acid in the heart muscle due to fatigue.

This condition is referred to as "ischemia". Ischemia not felt by the patient is generally referred to as "silent ischemia" while ischemia which is painful to the patient is generally referred to as "angina". It is very important, especially with silent ischemia, to monitor and accurately measure the ST level of the patient's normal heart beats in order to be able to properly diagnose and treat a patient with an ischemic condition.

Since the recorder 10 of the present invention identifies every normal beat during the beat classification process, each normal beat occurring on each of the 3 channels of ECG signals can be found and analyzed for ST depression and elevation. The recorder of the present invention performs this task as follows.

For each ECG signal channel, the QRS peak location is approximated from the point at which a beat is detected over the beat detection threshold as explained above. Then, the ST algorithm backs up 10 samples from the peak of the QRS complex to approximately land on the PR interval of the beat wave form. Next, a region of "minimum activity" is located and the baseline offset, identified as "Base Corr(i)" is found. The "minimum activity" region is found by finding the smaller of the two 3-point absolute value derivatives in a 5 sample window on the PR interval. The baseline offset is taken for the sample which is located 30 samples forward of the QRS peak which is thereafter identified as the ST segment. The baseline offset at the region of "minimum activity" is subtracted from the sample value at this point and, and the difference, measured in millimeters, is taken to be the ST level.

Each time an ST level is calculated, a "last eight beat" ST level average is also calculated. Each ST level average during the minute is compared to the last eight beat minimum and maximum ST level average to find the minimum and the maximum eight beat average for the minute. Hourly and monitoring period minimum and maximum ST levels are also determined in the above fashion.

ST level sums are also maintained in the minute summaries, hour summaries and the end of monitoring period summary, with the corresponding normal beat counts. The minute ST level averages are calculated by dividing the minute ST level sum by the normal beat counts during the minute. The hour ST level averages are also calculated in a similar fashion.

The minimum, maximum, and average ST levels are each stored as a signed byte of information. Each value is used along with the gain set for each channel and the analog to digital range set for each channel in order to calculate the ST depression or elevation value.

Since, the ST averages all require extensive computations, the computational load is spread over several periodic interrupt cycles. The minute averages are computed over the next three interrupt cycles from the minute boundary, and the hour averages are spread over three interrupt cycles in a similar manner. Since the end of period ST level average is calculated after completion of the monitoring period, when all other analyses have ended, there is little burden on the microcontroller 30 and the computations are done in a single interrupt cycle.

Any time an eight beat ST level average for a channel exceeds a previous minimum or maximum level, the "normal" beats containing the minimum and maximum ST level for each channel are transferred to a buffer and the time stamps for each beat is noted. An analog to digital conversion of the ECG waveform counting the minimum and maximum ST level is performed and the data is maintained in buffer for the entire monitoring period, with each successive ST level being compared to the minimum and maximum ST levels of the ECG waveforms contained in the buffer, and the buffer being overwritten with the new ECG waveform each time the minimum or maximum ST level is exceeded. The final minimum and maximum ST level beats become part of the end of monitoring period summary.

Minute ST level averages are monitored over the entire monitoring period to determine an ST "episode". An "episode" is detected if the minute ST level average in any channel is at least less than −1.0 mm and is sustained at this depressed level for more than a minute. ST episodes of less than −1.0 mm, −2.0 mm, and −3.0 mm and their duration time in minutes are recorded.

Other Recorded Parameters

Along with the above described beat morphologies and the information generated by the ST analysis, other parameters may be recorded onto the cassette tape 33 for use by the medical worker as evaluation and diagnostic tools. Among the other possible parameters are heart rate and patient initiated event marking.

For heart rate, 8 beat averages for high, low, and average heart rates are taken during a 24 hour period. Further, the recorder allows the medical worker to select heart rate ranges of 10 beat increments, from 80 to 240 beats per minute (bpm) for tagging beats above the selected bpm as tachycardia. The preferred default setting for tachycardia rate in the present invention is 120 bpm. Similarly, the medical worker can select rate criteria in 10 beat increments, from 20 to 80 bpm for the recorder 10 to tag bpm rates below the chosen bpm value as bradycardia, with the preferred default value for bradycardia being set at 40 bpm.

Also, the recorder 10 can identify beats as being "dropped beats", or "pauses". For example, should a delay between beats occur which is substantially equal to the absence of a single beat, the delay can be marked by the recorder 10 as a "dropped beat". Should a delay in beat detection occur over an interval of 1 second to 5 seconds, as preset by the medical worker, the recorder 10 can identify the time period as a "pause". With regard to the pauses, the recorder 10 is preferably preset to a default pause interval of 2 seconds.

Each of the above mentioned parameters are calculated by the recorder 10 and recorded on the digital data track 3 of the cassette 33.

Patient Event Marker

Whenever the patient event marker 20 is activated during the monitoring period, the tape 33 is simultaneously marked. It is intended that the patient use the event marker 20 in order to tag a particularly significant event or physical sensation. It is intended that the patient also record, such as in a diary, the specifics of the particular event which caused him or her to push the event marker 20, including the approximate time the button was pushed. Upon analysis, the medical worker can then review the diary in conjunction with information received from the recorder 10 for the same time period, to gain a better understanding of the patient's heart activity during the particular noted event.

Minute And Hour Summaries

Both the analog ECG signals and the digital analysis information are transferred from 4 data channels within the recorder 10 to the 4 data tracks on tape 33. The first and second channels contain the chosen two channels of analog ECG waveform data and are recorded onto Tracks 1 and 2 respectively of the tape 33, with the third set of analog ECG data (if present) not being recorded. The digital data comprising beat detection and ST analysis is recorded onto Track 3, and the clock data is recorded onto Track 4.

A set of beat classification data, comprising 4 bits of information, is recorded onto Track 3 of the cassette 33 for each classified beat. Three of the data bits of each set are used in classifying the beat as having a particular morphology classification type. The fourth bit is used as a start bit. For example, the classifications discussed above can be each defined using 3 data bits for purposes of classifying each beat in the following manner:

| Morphology | Bits |
|---|---|
| Unusable | 000 |
| Normal (N) | 001 |
| Abnormal (Ventricular) (V) | 010 |
| Learned (L) | 011 |
| Reserved | 100 |
| Cal-Pulse (C) | 101 |
| Paced (P) | 110 |
| Reserved | 111 |

As can be seen, there is the possibility of seven different beat morphologies being included in the classification process. As shown above however, a preferred embodiment of the invention may include five beat morphologies and two non-beat morphologies (i.e. "Learn" and "Cal-Pulse"). Alternatively, if desired, beats may be classified on a basis other than their morphology, or different beat morphologies may be used, such as "failure to sense" beats, "fusion beats" (i e., a beat occurring very closely after a pacer spike or even merging therewith), "strictly normal" "SVE normal" etc Also, a longer recording format of more than 4 bits may be used to record more than seven different morphology classifications if desired.

Each 4 bit data packet is encoded onto Track 3 of the tape in a position corresponding to the analog beat waveform recorded onto Tracks 1 and 2 using well known "return-to-zero" type tape formatting At the end of each minute of the test period, a summation of analysis data is recorded onto the tape 33. This minute summary data includes 27 bytes organizing the following information:

| Data | Data Size |
|---|---|
| Minute summary ID | 1 byte |
| Hour Number | 1 byte |
| Minute Number | 1 byte |
| Minimum ST level for channel 1 | 1 byte |
| Maximum ST level for channel 1 | 1 byte |
| Average ST level for channel 1 | 1 byte |
| Minimum ST time stamp for channel 1 | 1 byte |
| Maximum ST time stamp for channel 1 | 1 byte |
| Minimum ST level for channel 2 | 1 byte |
| Maximum ST level for channel 2 | 1 byte |
| Average ST level for channel 2 | 1 byte |
| Minimum ST time stamp for channel 2 | 1 byte |
| Maximum ST time stamp for channel 2 | 1 byte |
| Minimum ST level for channel 3 | 1 byte |
| Maximum ST level for channel 3 | 1 byte |
| Average ST level for channel 3 | 1 byte |
| Normal beats in a minute | 1 byte |
| SVE beats in a minute | 1 byte |
| Abnormal beats in a minute | 1 byte |
| Paced beats in a minute | 1 byte |

| Data | Data Size |
| --- | --- |
| Average R-R (heart rate) | 2 bytes |
| Noncaptured beats in a minute | 1 byte |
| Failure to sense beats in a minute | 1 byte |
| Noise events and patient events | 1 byte |
| Minute summary check sum | 2 bytes |

The minute summary information written at the end of each minute is actually analysis information collected in a buffer from the previous minute. The minute summary data is recorded onto Track 3 and Track 4 simultaneously and repetitively until the buffer is overwritten with new minute information from the next minute. This generates a redundancy of the minute summary information of 3 times per track, for a total of 6 times each minute. Because the minute summary data written to the tape 33 contains information that is "one minute old" two special cases emerge. The first case is when the analysis of ECG waveforms begins, the second case is when the monitoring period ends. In the first case, analysis of ECG waveform information begins at the beginning of the "learn" mode in the Initialization phase of operation. To allow for a smooth transition from calibration pulse recordation to patient pulse recordation, and to allow the calibration pulses to be recognized and readily identified by the screener, the first minute of data analysis actually begins during the "calibration" mode, with the beats detected being classified as calibration pulse beats (C). The end of the first minute, and subsequently the minute summary information generated therefore will and recorded to the tape 33 will contain valid minute summary information with all unrelated fields set to zero.

After the "calibration" mode is complete, the "learn" mode begins. During this mode, the minute summary information recorded to the tape 33 at the end of each minute will contain "learn" beats and pertinent minute summary information with all unrelated fields being set to zero.

When the monitoring period ends, the last minute summary information must still be written. Thus the length of Monitoring phase is therefore extended a sufficient time to allow the last minute summary information to be recorded to the tape 33. No further analysis of incoming ECG waveforms is performed during this time.

Because summary information data must be recoverable, the recorder 10 of the present invention preferably includes the use of an error correction/detection technique. The preferred form of error detection for the present invention is a 16 bit check sum. Also, each minute summary is recorded six times, three times on Track 3 and three times on Track 4 before the buffer holding the minute information is written over with summary information from the next minute.

The beginning of each down load of minute information from the buffer is used as a "marker" on the tape 33 to mark the exact location of each minute. This enables the playback deck of the scanner to enable or disable external hardware to allow or disallow sending data to the main system of the scanner. Because the minute summary information is not written until the minute it relates to is over, there will be a nearly constant phase delay between the time the RTC 29 indicates the beginning of a minute and the time the playback deck indicates the beginning of the same minute. This delay is the time required to read the time stamp for the minute and handle the electronic interrupts necessary in the scanner for receiving the information. The delay is only about 0.625 seconds and therefore is of no consequence except for the occasional slipping of an isolated beat from being counted in a previous minute to being counted in the next subsequent minute.

Hourly summaries are also compiled and collected at the end of each hour, and saved in an end of monitoring period summary buffer to be included in the end of monitoring period summary. Also at the end of the monitoring period, the max, min, and average ST levels are transferred to this buffer. Each hourly summary preferably includes 53 bytes of information as follows:

| Data | Data Size |
| --- | --- |
| Hour summary ID | 1 byte |
| Hour Number | 1 byte |
| Minimum ST level for channel 1 | 1 byte |
| Maximum ST level for channel 1 | 1 byte |
| Average ST level for channel 1 | 1 byte |
| Minimum ST level for channel 2 | 1 byte |
| Maximum ST level for channel 2 | 1 byte |
| Average ST level for channel 2 | 1 byte |
| Minimum ST level for channel 3 | 1 byte |
| Maximum ST level for channel 3 | 1 byte |
| Average ST level for channel 3 | 1 byte |
| Maximum R-R | 2 bytes |
| Minimum R-R | 2 bytes |
| Average R-R | 2 bytes |
| Number of patient events | 2 bytes |
| Number of noise events on channel 1 | 2 bytes |
| Number of noise events on channel 2 | 2 bytes |
| Number of noise events on channel 3 | 2 bytes |
| Number of artifact events | 2 bytes |
| Number of normal beats | 4 bytes |
| Number of SVE beats | 4 bytes |
| Number of abnormal beats | 4 bytes |
| Number of paced beats | 4 bytes |
| Number of noncaptured beats | 4 bytes |
| Number of failure to sense beats | 4 bytes |
| 16 bit checksum | 2 bytes |
| Break-Idle | 2 bytes |

Monitoring Period Summary

At the end of the monitoring period, the end of monitoring period summary buffer preferably has included therein the following data:

| |
| --- |
| Minimum ST wave forms |
| Minimum ST wave form header |
| Number of ST depression episodes and min/max R-R |
| Start/Stop, Time/Date, and Gain Setting |
| Individual hour summaries |

The minute ST waveforms each contain 156 bytes of information relating to the most precise digital reproduction of the analog form of the wave by the microcontroller 30. Due to its large size, each minimum ST waveform is broken up into eight sections to allow better data recovery in case of tape errors. The format of the data is as follows:

| Data | Data Size |
| --- | --- |
| Packet ID | 1 byte |
| Waveform ID | 2 bytes |
| Digital waveforms | 2 bytes |
| 16 bit checksum | 2 bytes |

Where the waveform ID contains the channel and section of the waveform, e.g. channel 1, 2, or 3; waveform section 0,1, 2, 3, 4, 5, 6, or 7.

Next included in the monitoring period summary buffer is the minimum ST waveform header which contains the header for the sample worst case ST data for each channel. The format of the minimum ST waveform header is as follows:

| Data | Data Size |
|---|---|
| Packet ID | 1 byte |
| Time of ST for channel 1 | 4 bytes |
| ST for channel 1 | 1 byte |
| ST point for channel 1 | 1 byte |
| Time of ST for channel 2 | 4 bytes |
| ST for channel 2 | 1 byte |
| ST point for channel 2 | 1 byte |
| Time of ST for channel 3 | 4 bytes |
| ST for channel 3 | 1 byte |
| ST point for channel 3 | 1 byte |
| 16 bit checksum | 2 bytes |
| Break-Idle | 2 bytes |

The time of ST is an offset time from the beginning of the monitoring period and is in the format of Hour: Minute: Second: Sample (HMSS).

The ST point for each channel is the number of samples included in the ST measurement (i.e., the measured width of the ST segment of the ECG waveform).

The next set of information in the monitoring period summary buffer is the number of ST depression episodes which includes the following information:

| Data | Data Size |
|---|---|
| Packet ID | 1 byte |
| Time of minimum ST channel 1 | 2 bytes |
| Time of maximum ST channel 1 | 2 bytes |
| Time of minimum ST channel 2 | 2 bytes |
| Time of maximum ST channel 2 | 2 bytes |
| Time of minimum ST channel 3 | 2 bytes |
| Time of maximum ST channel 3 | 2 bytes |
| Time of minimum heart rate | 2 bytes |
| Time of maximum heart rate | 2 bytes |
| ST (−1.02−1.9) duration | 2 bytes |
| ST (−1.02−1.9) episodes | 2 bytes |
| ST (−2.02−2.9) duration | 2 bytes |
| ST (−2.02−2.9) episodes | 2 bytes |
| ST (−3.0 +) duration | 2 bytes |
| ST (−3.0 +) episodes | 2 bytes |
| 16 bit checksum | 2 bytes |
| Break-Idle | 2 bytes |

Where the time is referred are offsets from the beginning of the monitoring period and are in the format of Hour: Minute (HM).

The ST duration information contains the number of minutes in which the ST level was in the specified range. The ST episode information contains the number of episodes in which the ST level was in the specified range.

The next set of information in the monitoring period summary buffer is a miscellaneous collection of information formatted as follows:

| Data | Data Size |
|---|---|
| Packet ID | 1 byte |
| Record gain selection channel 1 | 1 byte |
| Record gain selection channel 2 | 1 byte |
| Record gain selection channel 3 | 1 byte |
| Calibration start time | 5 bytes |
| Monitoring period start time | 5 bytes |
| Monitoring period stop time | 5 bytes |
| 64 bit recorder specific data | 8 bytes |
| 16 bit checksum | 2 bytes |
| Break-Idle | 2 bytes |

Where the times are written in the format of Month: Day: Year: Hour: Minute (MDYHM).

The 64 bit recorder specific data includes data and other information to describe the recorder 10. The purpose for collecting this information is to allow future compatibility of the recorded information with future instrumentation which may be used to read and manipulate the data from the tape 33. An example of data that may be included in this information could be a software version number, recorder model number, etc. Any space unused in this 64 bit field will be placed at zero.

Similar data format and error correction/detection techniques used for the minute summary information is also used for the end of monitoring period summary information. The end of period summary is recorded on Tracks 3 and 4 of the tape 33 simultaneously and repeated three times. Thus, the monitoring period summary will be recorded to the tape 33 a total of six times.

As has been stated above, after completion of the entire monitoring period, the recorder 10 continues to operate to compile and record the end of monitoring period summary information. During this time, incoming ECG signal waveforms are output to Tracks 1 and 2 of the tape 33, but are ignored by the microcontroller 30 for purposes of analysis. Only the end of period summary information is output from the microcontroller 30 onto Tracks 3 and 4 of the tape 33 during this time. The end of period summary information is collected from the end of monitoring period summary buffer which may contain the above-identified information in a standard digital format, or may have received the information from the microcontroller 30 in a reverse order compared with the standard digital format. The information in the buffer is divided into a series of bytes of information, with each byte including a series of bits of information. Each byte consists of a start bit, a series of data bits (usually eight) and a stop bit.

This type of digital information is commonly transmitted to the recording head of a recorder in a very rapid manner through a standard UART (Universal Asynchronsis Receiver Transmitter). The UART receives each data bit in parallel format and outputs them to the recording head in serial format to form an information byte, including a start bit followed by the data bits and a stop bit.

However, the end of period summary information of the present invention is output to the recording head 32 of the recorder 10 with the data bits, including the start bit and stop bit, in reverse order, so that the information is recorded onto tape 33 with the stop bit recorded first and the data bits recorded secondly (in reverse order) followed lastly by the start bit. Each byte of information is recorded to the tape 33 from the end of period summary information buffer in this manner.

It should be noted that the buffer may receive the information bytes in reverse order from the microcontroller 30, in which case the information would be withdrawn from the buffer beginning with the first byte of information and ending with the last byte, or alternatively, the information byte may be received by the buffer in forward order, in which case the bytes of information would be withdrawn from the buffer beginning with the last information byte therein and ending with the first information byte. In either case, the bytes of information leave the buffer in reverse order, and proceed thereafter to have their individual bits reversed prior to being recorded to the tape 33.

It should be further noted at this point that the end of period summary buffer is preferably organized so that the most important information collected during the monitoring period will record onto tape 33 as early as possible, in case the recorder 10 is inadvertently stopped prior to complete downloading of the summary information onto the tape 33.

Since it is impossible for a UART to serially output a set of data bits representing a byte of information with the bits in reverse order, i.e., with a stop bit preceding and a start bit following the reversed data bits, the present invention passes the end of monitoring period summary information directly from the buffer through the microcontroller 30 and "toggles" the microcontroller 30 through the incoming lines of data to effect a serial transmission of a stop bit followed by a reverse order set of data bits and a start bit for each byte of information as it passes therethrough. Thus, as the information from the buffer is downloaded through the microcontroller 30, the data bits in each byte of information are reversed, including the start and stop bits, and recorded simultaneously onto Tracks 3 and 4 of the tape 33.

At the time of the downloading of information from the end of period summary information buffer to the tape 33, there are no other demands on the microcontroller 30, since the monitoring period has ended and no further information is being collected or analyzed. This low load on the microcontroller 30 during reverse recording of the end of period summary information makes it possible to route the information for reverse recording through the microcontroller 30 in a relatively rapid manner, even though this manner of processing the information is extremely slow compared to the standard UART processing speed.

As is readily evident, subsequent rewinding of the tape 33 in a playback deck of a scanner, with the tape passing the playback head in a reverse direction, will allow the reverse recorded summary information thereon to be received through the playback head in its proper (forward) order for serial input into a standard UART in the playback deck. The result being that the playback deck UART will receive a start bit followed by the properly ordered data bits and a stop bit. The UART can therefore recognize the information and properly decode it for parallel output and processing by the scanner.

Once a monitoring period is completed and the end of period summary information is reverse recorded onto the tape 33, a medical worker need only insert the tape 33 into a playback deck of the scanner and initiate rewinding of the tape 33 for review. Immediately upon initiation of the rewind, the playback deck will immediately begin to read the end of period summary information, since it is passing by the playback deck head in the forward direction. Once the entire end of period summary information has been read, the tape 33 will continue to rewind. Simultaneously with the continued rewind of the tape 33, the scanner can process the already received end of period summary information to generate a summary report of pertinent information collected during the monitoring period for the medical worker's review, even before the tape 33 has completely rewound. In this manner, a medical worker may receive summary information collected during a monitoring period within two to three minutes of initiating rewind of the tape 33, and even prior to or without any necessity of downloading the bulk of information collected on the tape 33 during the monitoring period.

It will be apparent from the foregoing, while particular embodiments of the invention have been illustrated and described, various modifications can be made thereto without departing from the spirit and scope of the present invention. Accordingly, it is not intended that the invention be limited, accept as by the appended claims.

What is claimed is:

1. A recorder for recording information onto a tape, at least a portion of the information including data related to analog ECG signals, said recorder comprising:
    means for receiving the information, and
    means for recording at least a portion of the information onto the tape in a reverse format.

2. A recorder according to claim 1 further including means for performing real-time analyses on the ECG signals, and said means for recording in said reverse format further includes means for recording data relating to said real-time analyses in said reverse format.

3. A recorder according to claim 2 wherein said means for recording further includes means for selecting and recording at least a portion of the information onto the tape in a forward format, including means for analog recording of at least a selected portion of the information and means for digital recording of at least a selected portion of the data relating to said real-time analyses.

4. A recorder according to claim 1 further including means for rotating the tape in a forward direction and wherein said means for recording in said reverse format operates while said means for rotating the tape rotates the tape in a forward direction.

5. A recorder according to claim 1 further including means to convert analog signals to digital signals and wherein at least a portion of the analog ECG signals received by said recorder are converted to digital ECG signals by said means for converting, and said means for recording in a reverse format further includes recording said digital ECG signals to the tape in said reverse format.

6. A recorder according to claim 1 further including buffer means which includes means for arranging the information in a series of bytes which each include a series of bits of data, and said means for recording in said reverse format includes recording each byte in said buffer means to the tape in series beginning from the last byte contained in said buffer means and ending with the first byte contained in said buffer means, each byte being recorded by said means for recording to the tape in series beginning with the last bit of data contained in the byte and ending with the first bit of data contained in the byte.

7. A recorder according to claim 1 further including buffer means for containing at least a portion of the information and means for placing said at least a portion of the information in said buffer means in a predetermined order, said recorder further including means for retrieving information from said buffer means in reverse order from said predetermined order, said means for recording in said reverse format including recording the information to the tape in said reverse order.

8. A recorder according to claim 1 wherein the information recorded in said reverse format by said means for recording is recorded by said means for recording onto the tape a plurality of times.

9. A recorder according to claim 1 wherein the information recorded in said reverse format by said means for recording is recorded by said means for recording to a plurality of tracks on the tape.

10. A recorder according to claim 1 wherein the information recorded in said reverse format by said means for recording is recorded by said means for recording onto a plurality of tracks of the tape simultaneously and repetitively.

11. A recorder for recording information onto a tape, at least a portion of the information including data related to analog ECG signals, said recorder including a recording head capable of transferring information to the tape as the tape passes thereover in a forward direction, said recorder comprising:
  means for receiving the information,
  means for transferring the information from said recorder to the tape including:
    forward format recording means for selecting and transferring a first portion of the information from said recorder to the tape in a forward format as the tape passes over said recording head in a forward direction, and
    reverse format recording means for selecting and transferring a second portion of the information from said recorder to the tape in a reverse format as the tape is moved past said recording head in said forward direction, at least a portion of said second portion of information selected and recorded in said reverse format by said reverse format recording means including at least a portion of the data related to the ECG signals.

12. A recorder according to claim 11 further including means for performing real-time analyses on the ECG signals, and said means for transferring the information from said recorder to the tape further includes means for transferring data relating to said real-tim analyses.

13. A recorder according to claim 12 wherein said means for transferring the information from said recorder to the tape further includes recording at least a portion of the data relating to said real-time analyses.

14. A recorder according to claim 11 further including buffer means which includes means for arranging the information in a series of bytes which each include a series of bits of data, and said reverse format recording means transfers each byte in said buffer means to the tape in series beginning from the last byte contained in said buffer means and ending with the first byte contained in said buffer means, each byte being transferred by said means for transferring to the tape in series beginning with the last bit of data contained in the byte and ending with the first bit of data contained in the byte.

15. A recorder according to claim 11 further including buffer means for containing at least a portion of the information and means for placing said at least a portion of the information in said buffer means in a predetermined order, said means for transferring the information from said recorder to the tape further including means for retrieving information from said buffer means in reverse order from said predetermined order, said reverse format recording means for recording in said reverse format including recording the information to the tape in said reverse order.

16. A recorder according to claim 11 wherein the information transferred by said reverse format means is transferred by said means for transferring onto the tape a plurality of times.

17. A recorder according to claim 11 wherein the information transferred by said means for transferring by said reverse format recording means is transferred to a plurality of tracks on the tape.

18. A recorder according to claim 11 wherein the information transferred by said means for transferring by said reverse format recording means is transferred onto a plurality of tracks of the tape simultaneously and repetitively.

19. A system for recording and playing back information related to ECG signals from a tape, including a recording means and a playback means, said system comprising:
  recording means including:
    means for receiving the information, and
    means for recording at least a portion of the information onto the tape in a reverse format as the tape is rotated in a forward direction in said recorder, at least a portion of the information recorded in said reverse format including at least a portion of the data related to the ECG signals, and
  playback means including:
    means for playing back the information recorded in said reverse format while the tape is rotated in a reverse direction in the playback means, and
    means for receiving said played back information including user interface means for allowing access to said played back information by a user.

20. A recorder according to claim 19 further including means for converting analog signals into digital signals and wherein at least a portion of the analog ECG signals received by said recorder are converted to digital ECG signals by said means for converting, and said means for recording further includes recording said digital ECG signals to the tape.

21. A recorder according to claim 19 wherein the information recorded in said reverse format is recorded by said means for recording onto the tape a plurality of times.

22. A recorder according to claim 19 wherein the information recorded in said reverse order is recorded by said means for recording to a plurality of tracks on the tape.

23. A recorder according to claim 19 wherein the information recorded in said reverse format is recorded by said means for recording onto a plurality of tracks of the tape simultaneously and repetitively.

24. A recorder according to claim 19 further including means for performing real-time analyses on the ECG signals, and said means for recording at least a portion of the information onto the tape in a reverse format further includes recording data relating to said real-time analyses.

25. A recorder according to claim 19 wherein said means for recording further includes recording at least a portion of the information onto the tape in a forward format as the tape is rotated in a forward direction in the recorder, including analog recording of at least a portion of the information and digital recording of at least a portion of the data relating to said real-time analyses,
  whereby said playback means further including means for playing back the information recorded in said forward format while the tape is rotated in a forward direction in the playback means.

26. A recorder according to claim 19 further including buffer means which includes means for arranging the information in a series of data bytes which each include a series of bits of data, and said means for recording in said reverse format includes recording each byte in said buffer means to the tape in series beginning from the last byte contained in said buffer means and ending with the first byte contained in said buffer means, each byte being recorded by said means for recording to the tape in series as the tape moves in said forward direction in said recorder beginning with the last bit of data contained in the byte and ending with the first bit of data contained in the byte.

27. A recorder according to claim 19 further including buffer means for containing at least a portion of the information and means for placing said at least a portion of the information in said buffer means in a predetermined order, said recorder further including means for retrieving information from said buffer means in reverse order from said predetermined order, said means for recording in said reverse format including recording the information to the tape in said reverse order as the tape is rotated in a forward direction in said recorder.

28. A recorder for use with an ambulatory ECG recording system, said recorder comprising:
  means for receiving analog ECG signals from an ambulatory patient,
  means for recording said analog ECG signals to a tape,
  means for performing real-time analysis on said analog ECG signals, and
  means for recording data related to said real-time analysis onto the tape, said means for recording said data including means for recording at least a portion of said data to the tape in a reverse format compared with the remainder of said data.

29. A recorder according to claim 28 further including means for rotating the tape in a forward direction and wherein said means for recording in said reverse format operates while said means for rotating the tape rotates the tape in a forward direction.

30. A recorder according to claim 28 further including means for converting analog signals into digital signals and wherein at least a portion of the analog ECG signals received by said recorder are converted to digital ECG signals by said means for converting, and said means for recording in a reverse format further includes a recording said digital ECG signals to the tape in said reverse format.

31. A recorder according to claim 28 further including buffer means which includes means for arranging the information in a series of bytes which each include a series of bits of data, and said means for recording in said reverse format includes recording each byte in said buffer means to the tape in series beginning from the last byte contained in said buffer means and ending with the first byte contained in said buffer means, each byte being recorded by said means for recording to the tape in series beginning with the last bit of data contained in the byte and ending with the first bit of data contained in the byte.

32. A recorder according to claim 28 further including buffer means for containing at least a portion of the information and means for placing said at least a portion of the information said buffer means in a predetermined order, said recorder further including means for retrieving information from said buffer means in reverse order from said predetermined order, said means for recording in said reverse format including recording the information to the tape in said reverse order.

33. A recorder according to claim 28 wherein the information recorded in said reverse format is recorded by said means for recording onto the tape a plurality of times.

34. A recorder according to claim 28 wherein the information recorded in said reverse order is recorded by said means for recording to a plurality of tracks on the tape.

35. A recorder according to claim 28 wherein the information recorded in said reverse format is recorded by said means for recording onto a plurality of tracks of the tape simultaneously and repetitively.

36. A method of recording information onto a tape for use in ECG analyses, at least a portion of the information including data related to ECG signals, said method including the steps of:
  collecting information for use in ECG analyses, at least a portion of which includes data related to ECG signals,
  recording at least a portion of the information for use in the ECG analyses onto the tape in a reverse format, at least a portion of the information recorded in said reverse format including at least a portion of the data related to the ECG signals.

37. A method according to claim 36 wherein said step of recording information in a reverse format includes the step of recording the information while the tape is operating in the forward direction.

38. A method according to claim 36 further including the step of:
  performing a real-time digital analysis on at least a portion of the information for use in the ECG analyses received by the recorder, and recording at least a portion of the digital data generated by the real-time analysis onto the tape in the reverse format for use in the ECG analyses.

39. A method according to claim 38 further including the step of producing digital data which includes a series of bytes of information in which each byte of information includes a series of bits of data, and said step of recording the information in a reverse format further includes recording the series of bytes of information reverse order and recording the bits of data in each byte in reverse order.

40. A method according to claim 36 further including the step of converting at least a portion of the data relating to ECG signals received by the recorder to digital ECG data, and said step of recording further includes recording at least a portion of said digital ECG data to the tape in the reverse format.

41. A method according to claim 36 wherein the recorder further includes a buffer means and said method further includes placing at least a portion of the information into the buffer means and said step of recording information in a reverse format includes retrieving at least a portion of the information from the buffer means.

42. A method according to claim 41 wherein said step of placing information into the buffer means includes placing a series of bytes of information into the buffer means such that the order of the bytes in the series is reversed.

43. A method according to claim 41 wherein the step of retrieving the bytes from the buffer means includes rearranging the bits of data of each byte into reverse order.

44. A method according to claim 41 wherein said step of retrieving the information from the buffer means includes removing the bytes in series beginning from the first byte of information in the buffer means and ending with the least byte of information in the buffer means.

45. A method according to claim 41 wherein said step of retrieving data from the buffer means includes removing bytes of information therefrom in series beginning from the last byte of information contained in the buffer means and ending with the first byte of information contained in the buffer means.

46. A method according to claim 36 wherein said step of recording information in reverse format includes the step of recording analysis information related to the ECG signals.

47. A method according to claim 46 wherein the tape includes a plurality of data tracks and said step of recording analysis information includes recording the information in reverse format onto the plurality of data tracks of the tape.

48. A method according to claim 46 wherein the step of recording analysis information onto the tape includes recording the analysis information a plurality of times.

49. A method according to claim 46 wherein the tape includes at least two data tracks and said step of recording analysis information includes recording the analysis information a plurality of times on each of at least two tracks of the tape.

50. A method according to claim 46 wherein the tape includes at least two data tracks and said step of recording analysis information includes recording the analysis information a plurality of times on each of at least two tracks of the tape.

51. A method of operating an ECG monitoring system having a recorder means which includes means for collecting information and a recording head; and a playback means including a playback head, the method comprising the steps of:
collecting information with the recorder means, at least a portion of the information including data related to ECG signals,
recording at least a portion of the collected information in a reverse format onto a tape while the tape moves in a forward direction over the recording head,
transferring the tape form the recording means to the playback means, and
playing back the information on the tape recorded in the reverse format while the tape moves past the playback head of the playback means in a reverse direction.

52. A method according to claim 51 further including the steps of:
recording at least a portion of the collected information in a forward format onto the tape while the tape moves in a forward direction over the recording head in the recorder, and
playing back the information on the tape recorded in the forward format while the tape moves past the playback head of the playback means in the forward direction.

53. A method according to claim 51 further including the step of:
performing a real-time digital analysis on at least a portion of the information for use in the ECG analyses received by the recorder, and recording at least a portion of the digital data generated by the real-time analysis onto the tape in the reverse format for use in the ECG analyses.

54. A method according to claim 53, further including the step of producing digital data which includes a series of bytes of information in which each byte of information includes a series of bits of data, and said step of recording the information in a reverse format further includes recording the series of bytes of information in reverse order and recording the bits of data in each byte in reverse order.

55. A method according to claim 51 further including the step of converting at least a portion of the data relating to ECG signals received by the recorder to digital ECG data, and said stp of recording further includes recording at least a portion of said digital ECG data to the tape in the reverse format.

56. A method according to claim 51 wherein the recorder further includes a buffer means and said method further includes placing at least a portion of the information into the buffer means and said step of recording information in a reverse format includes retrieving at least a portion of the information from the buffer means.

57. A method according to claim 56 wherein said step of placing information into the buffer means includes placing a series of bytes of information into the buffer means such that the order of the bytes in the series is reversed.

58. A method according to claim 56 wherein the step of retrieving the bytes from the buffer means includes rearranging the bits of data of each byte into reverse order.

59. A method according to claim 56 wherein said step of retrieving the information from the buffer means includes removing the bytes in series beginning from the first byte of information the buffer means and ending with the last byte of information the buffer means.

60. A method according to claim 56 wherein the buffer means includes a series of bytes of information and said step of retrieving data from the buffer means includes removing bytes of information therefrom in series beginning from the last byte of information contained in the buffer means and ending with the first byte of information contained in the buffer means.

61. A method according to claim 51 wherein said step of recording information in reverse format includes the step of recording analysis information related to the ECG signals.

62. A method according to claim 61 wherein the tape includes a plurality of data tracks and said step of recording analysis information includes recording the information in reverse format onto the plurality of data tracks of the tape.

63. A method according to claim 61 wherein the step of recording summary information onto the tape includes recording the summary information a plurality of times.

* * * * *